(12) United States Patent
Shoshtaev et al.

(10) Patent No.: US 11,672,573 B2
(45) Date of Patent: Jun. 13, 2023

(54) APPARATUS AND METHOD OF TREATING SPINOUS PROCESSES

(71) Applicant: Spinal Elements, Inc., Carlsbad, CA (US)

(72) Inventors: Eugene Shoshtaev, Del Mar, CA (US); Roberto Monterroso, Encinitas, CA (US); Jason Blain, Encinitas, CA (US); Forrest Samuel, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 14/935,276

(22) Filed: Nov. 6, 2015

(65) Prior Publication Data

US 2016/0228157 A1    Aug. 11, 2016

Related U.S. Application Data

(60) Provisional application No. 62/076,412, filed on Nov. 6, 2014.

(51) Int. Cl.
*A61B 17/70* (2006.01)
*A61B 17/56* (2006.01)
*A61B 17/68* (2006.01)

(52) U.S. Cl.
CPC .... *A61B 17/7068* (2013.01); *A61B 2017/564* (2013.01); *A61B 2017/681* (2013.01); *A61B 2017/7073* (2013.01)

(58) Field of Classification Search
CPC ........... A61B 17/7062–7068; A61B 2017/681; A61B 2017/7073; A61F 2/4405

USPC ................................................. 606/248–249
See application file for complete search history.

(56) References Cited

U.S. PATENT DOCUMENTS

| | | |
|---|---|---|
| 2,677,369 A | 5/1954 | Knowles |
| 3,030,951 A | 4/1962 | Mandarino |
| 5,496,318 A | 3/1996 | Howland et al. |
| 5,645,599 A | 7/1997 | Samani |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |

(Continued)

FOREIGN PATENT DOCUMENTS

| | | |
|---|---|---|
| JP | 2012228612 | 11/2012 |
| JP | 2013504384 | 2/2013 |
| WO | 2014/078798 | 5/2014 |

OTHER PUBLICATIONS

International Search Report and Written Opinion for International Application No. PCT/US2015/059582, dated Mar. 29, 2016.

(Continued)

*Primary Examiner* — Nicholas J Plionis

(57) ABSTRACT

An interspinous process device includes a first plate, a second plate, and a transverse member between the first plate and the second plate, wherein the second plate is adjustably coupled to the transverse member. A post is coupled to the transverse member and a spring mechanism is disposed between the post and the first plate. The spring mechanism is configured to provide a preloaded compression force to the first and second plates. Methods of implanting the interspinous process device using an inserter tool are also disclosed.

19 Claims, 21 Drawing Sheets

(56) References Cited

U.S. PATENT DOCUMENTS

| | | |
|---|---|---|
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,238,397 B1 | 5/2001 | Zucherman et al. |
| 6,478,796 B2 | 11/2002 | Zucherman et al. |
| 6,695,842 B2 | 2/2004 | Zucherman et al. |
| 7,048,736 B2 | 5/2006 | Robinson et al. |
| 7,087,083 B2 | 8/2006 | Pasquet et al. |
| 7,727,233 B2 | 6/2010 | Slackwell et al. |
| 8,241,330 B2 | 8/2012 | Lamborne et al. |
| 8,343,190 B1 * | 1/2013 | Mueller ............ A61B 17/7068 606/248 |
| 8,382,801 B2 | 2/2013 | Lamborne et al. |
| 8,419,738 B2 | 4/2013 | Smisson, III et al. |
| 8,591,547 B2 | 11/2013 | Smisson, III et al. |
| 9,211,147 B2 | 12/2015 | Gordon |
| 9,668,786 B2 | 6/2017 | Field et al. |
| 2004/0181285 A1 | 9/2004 | Simonson |
| 2006/0106381 A1 | 5/2006 | Ferree et al. |
| 2006/0235391 A1 * | 10/2006 | Sutterlin ............ A61B 17/7064 606/86 A |
| 2006/0247634 A1 | 11/2006 | Warner et al. |
| 2007/0093823 A1 | 4/2007 | Booth et al. |
| 2008/0183211 A1 | 7/2008 | Lamborne et al. |
| 2010/0318127 A1 * | 12/2010 | Phan ................ A61B 17/7065 606/249 |
| 2011/0066186 A1 | 3/2011 | Boyer, II et al. |
| 2011/0166600 A1 * | 7/2011 | Lamborne ......... A61B 17/7068 606/249 |
| 2011/0172711 A1 * | 7/2011 | Kirschman ........ A61B 17/7068 606/252 |
| 2011/0264221 A1 | 10/2011 | Woodward et al. |
| 2011/0319936 A1 | 12/2011 | Gordon et al. |
| 2012/0089184 A1 | 4/2012 | Yeh |
| 2012/0232592 A1 | 9/2012 | Massoudi |
| 2012/0253393 A1 | 10/2012 | Fiorella |
| 2012/0259366 A1 * | 10/2012 | Lange ............... A61B 17/7067 606/248 |
| 2013/0190820 A1 * | 7/2013 | Siegfried .......... A61B 17/7068 606/248 |
| 2013/0226240 A1 * | 8/2013 | Abdou .............. A61B 17/7067 606/248 |
| 2013/0296939 A1 * | 11/2013 | Perkins ............. A61B 17/7068 606/249 |
| 2013/0338712 A1 * | 12/2013 | Massenzio ........ A61B 17/7014 606/252 |
| 2014/0277144 A1 | 9/2014 | Aschmann et al. |

OTHER PUBLICATIONS

Extended European Search Report for European Application No. 15857134.9, dated Jun. 11, 2018.

Extended European Search Report for European Application No. 22156200.

\* cited by examiner

APPARATUS AND METHOD OF TREATING SPINOUS PROCESSES

CROSS-REFERENCE TO RELATED APPLICATIONS

The present application claims priority benefit under 35 U.S.C. § 119(e) of U.S. Provisional Application No. 62/076,412, filed Nov. 6, 2014, the content of which is incorporated by reference herein in its entirety.

BACKGROUND

Field

The present application relates to spinal surgery, and more particularly to devices and methods for stabilization of the spinous processes of the spine.

Related Art

The spinal structure can become damaged as a result of degeneration, dysfunction, disease and/or trauma. More specifically, the spine may exhibit disc collapse, abnormal curvature, asymmetrical disc space collapse, abnormal alignment of the vertebrae and/or general deformity, which may lead to imbalance and tilt in the vertebrae. This may result in nerve compression, disability and overall instability and pain. If the proper shaping and/or curvature are not present due to scoliosis, neuromuscular disease, cerebral palsy, or other disorder, it may be necessary to straighten or adjust the spine into a proper curvature with surgery to correct these spinal disorders.

The current standard of care to address the degenerative problems is to fixate the two adjacent vertebrae. The adjacent vertebrae can be fixed and distracted by treating the spinous processes. Fixation is a surgical method wherein two or more vertebrae are held together by the placement of screws, rods, plates, and/or cages to stabilize the vertebrae. In many cases, the fixation is augmented by a process called fusion, whereby an implant is placed in the intervertebral space between two or more vertebrae to join the vertebrae together.

By performing this surgical procedure, the relative motion between the two spinous processes is stopped, thus stopping motion of the vertebrae and any potential pain generated as a result thereof. Current procedures to fixate and/or stabilize adjacent spinous processes and/or other bones, however, can be slow and/or complex. Accordingly, a need exists for an apparatus and methods to better stabilize and/or fixate the spinous processes.

INCORPORATION BY REFERENCE

All publications and patent applications mentioned in this specification are herein incorporated by reference to the same extent as if each individual publication or patent application was specifically and individually indicated to be incorporated by reference.

SUMMARY

An aspect of at least one of the embodiments disclosed herein includes an interspinous process device including a first plate having a through hole, a second plate having an aperture, and a transverse member disposed between the first plate and the second plate, wherein the transverse member is configured to fit through the aperture of the second plate and the second plate is adjustably securable to the transverse member. The interspinous process device can also include a post disposed through the hole in the first plate and coupled to the transverse member, and a spring mechanism disposed between the post and the first plate, the spring mechanism configured to provide a preloaded force to the first plate.

In some embodiments, a first surface of the transverse member has an angle with respect to a second opposite surface of the transverse member. The angle can be at least approximately 0.1 degree and/or less than or equal to approximately 3 degrees. The angle can be approximately 0.7 degree.

In some embodiments, the spring mechanism is comprised of at least one beveled washer. In other embodiments, the spring mechanism is comprised of a helical spring or an elastomeric material.

In some embodiments, the post comprises a head with anti-rotational features configured to engage the first plate.

An aspect of at least one of the embodiments disclosed herein includes an interspinous process device including a first plate, a second plate, a transverse member between the first plate and the second plate, wherein the second plate is adjustably coupled to the transverse member, and a spring mechanism configured to provide a preloaded compression force to the first and second plates.

In some embodiments, the interspinous process device further includes a post coupled to the transverse member, wherein the spring mechanism is disposed between the post and first plate. The post can include a head with anti-rotational features configured to engage the first plate.

In some embodiments, the interspinous process device further includes a fastener on the second plate that tightens on the transverse member. The second plate can be configured to pivot about the fastener.

In some embodiments, the transverse member includes an orifice configured to receive bone growth material. The first plate and the second plate can have a plurality of spikes configured to engage bone.

In some embodiments, a first surface of the transverse member has an angle with respect to a second opposite surface of the transverse member. The angle can be at least approximately 0.1 degree and/or less than or equal to approximately 7 degrees. The angle can be at least approximately 0.1 degree and/or less than or equal to approximately 3 degrees. In some embodiments, the angle is approximately 0.7 degree.

In some embodiments, the spring mechanism is comprised of at least one beveled washer. The spring mechanism can be comprised of a helical spring. The spring mechanism can be comprised of an elastomeric material. In some embodiments, at least a portion of the device has a coating made of one or more of titanium and hydroxylapatite.

An aspect of at least one of the embodiments disclosed herein includes a method of implanting an interspinous process device, including: delivering an assembly between a superior spinous process and an inferior spinous process, the assembly comprising a first plate, a spring mechanism and a transverse member coupled to the first plate, wherein the assembly is delivered laterally such that the transverse member is inserted in the interspinous space and the first plate is adjacent a first side of the spinous processes; delivering a second plate to a second side of the spinous processes and mounting the second plate to the transverse member; applying a preload to the spring mechanism; compressing the first plate and the second plate together while applying the preload to the spring mechanism; and actuating a fastener to lock the second plate to the transverse member.

In some embodiments, the method further includes delivering a bone growth material into the transverse member. The first plate and the second plate can have spikes that couple with the spinous processes when compressing the first plate and the second plate together. The transverse member can be inserted in the interspinous space in a first orientation and then rotated to a second orientation.

An aspect of at least one of the embodiments disclosed herein includes a method of implanting an interspinous process device, comprising: delivering an assembly between a superior spinous process and an inferior spinous process, the assembly comprising a first plate, a second plate, a spring mechanism and a transverse member coupled to the first plate and the second plate, wherein the assembly is delivered from a posterior approach in a first orientation; rotating the assembly in the implant site to a second orientation; applying a preload to the spring mechanism; compressing the first plate and the second plate together while applying the preload to the spring mechanism; and actuating a fastener to lock the second plate to the transverse member.

In some embodiments, the method further comprises delivering a bone growth material into the transverse member. The first plate and the second plate can have spikes that couple with the spinous processes when compressing the first plate and the second plate together. In some embodiments, when the assembly is rotated to the second orientation, the spinous processes are distracted.

BRIEF DESCRIPTION OF THE DRAWINGS

These and other features, aspects and advantages of the described embodiments are described with reference to drawings of certain preferred embodiments, which are intended to illustrate, but not to limit. It is to be understood that the attached drawings are for the purpose of illustrating concepts of the described embodiments and may not be to scale.

DETAILED DESCRIPTION

As will be explained herein, certain embodiments of interspinous process devices, methods and related tools provide advantages over the prior art devices. For example, the interspinous process device of the illustrated embodiment can have plates that are preloaded with compressive loads to account for loosening of the device after implantation. Methods and related tools for delivering, implanting and fixing the disclosed preloaded interspinous process devices are also disclosed.

Figure 1:
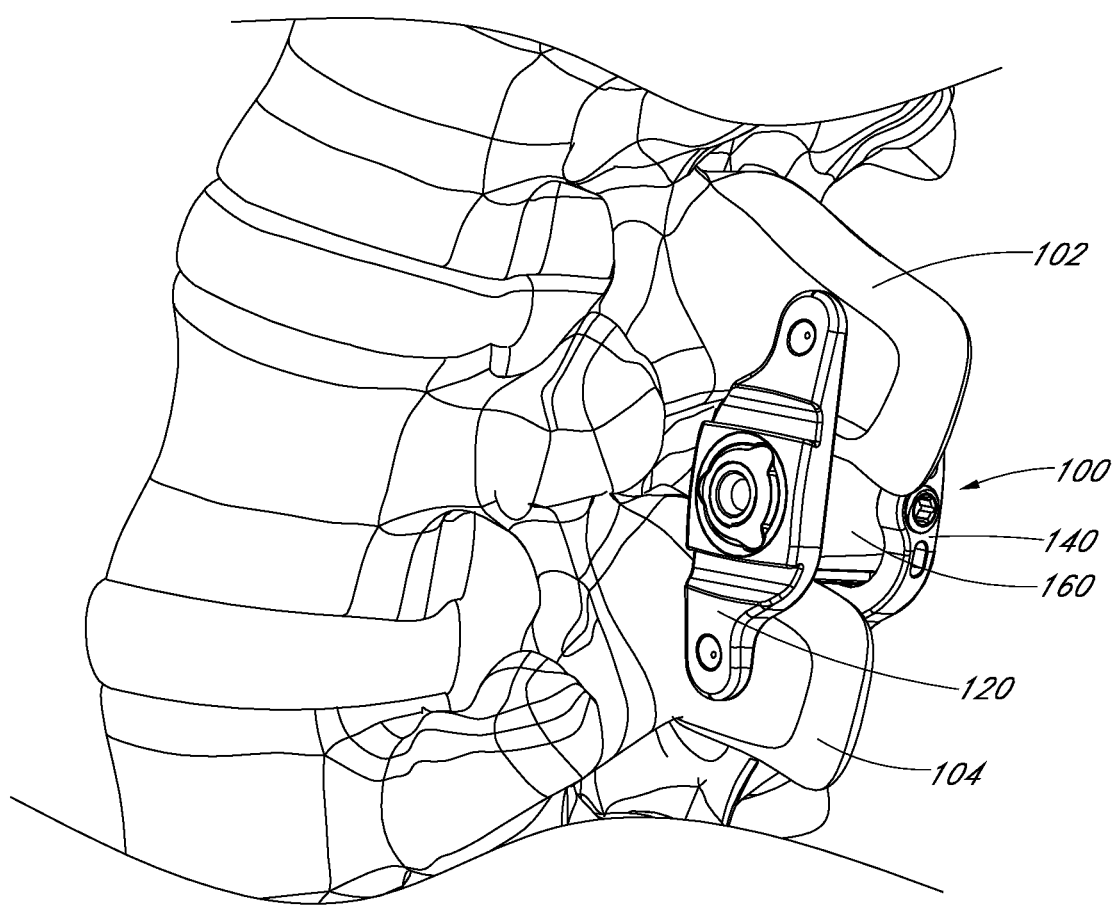
FIG. 1 is a perspective view of an interspinous process device implanted in a spine, according to an embodiment of the present disclosure.

FIG. 1 illustrates an interspinous process device 100 implanted between a superior spinous process 102 and an inferior spinous process 104. The device 100 can comprise a first plate 120 configured to span from the superior spinous process 102 to the inferior spinous process 104. The device 100 can also comprise a second plate 140 configured to span from the superior spinous process 102 to the inferior spinous process 104. A transverse member 160 can be disposed between the first plate 120 and the second plate 140 and can be configured for placement in the interspinous space. In some embodiments, the transverse member 160 is a spacer that can contact one or both of the superior spinous process 102 and the inferior spinous process 104, as illustrated in FIG. 1. In other embodiments, the transverse member can be any of a plurality of different types of connecting members, such as a solid rod, and may not contact either or both of the spinous processes.

The first plate 120 can couple to one side of the spinous processes 102, 104 and the second plate 140 can couple to an opposite side of the spinous processes 102, 104. The first plate 120 and second plate 140 can be brought together to clamp onto and stabilize the spinous processes 102, 104. As illustrated in FIG. 1, the first plate 120 and the second plate 140 can clamp onto an inferior portion of the superior spinous process 102 and a superior portion of the inferior spinous process 104. In some embodiments, the first plate 120 and/or second plate 140 can include spikes, ridges, hooks, or other features to engage the spinous processes 102, 104.

The transverse member 160 can be wide enough to contact the inferior surface of the superior spinous process 102 and the superior surface of the inferior spinous process 104. In some embodiments, the transverse member 160 is wide enough to distract the spinous processes apart to open the intervertebral foramen for treatment of spinal stenosis or other spinal condition. In some embodiments, the transverse member 160 helps maintain the proper spacing between the spinous processes 102, 104.

Multiple interspinous process devices 100 can be part of a kit that includes transverse members 160 with a plurality of different widths. An interspinous process device 100 having a transverse member 160 with a desired width for a specific patient's anatomy can be selected from the kit. In some embodiments, the interspinous process device has a transverse member that is expandable, where the width of the transverse member is adjustable to fit a range of patient anatomies. The expandable transverse member can have an expansion mechanism that is actuated after implanting between a superior spinous process and an inferior spinous process. The expandable transverse member can be expanded until it contacts the inferior surface of the superior spinous process 102 and the superior surface of the inferior spinous process 104. In some embodiments, the expandable transverse member is used to distract the superior spinous process 102 and the inferior spinous process 104.

Figure 2:
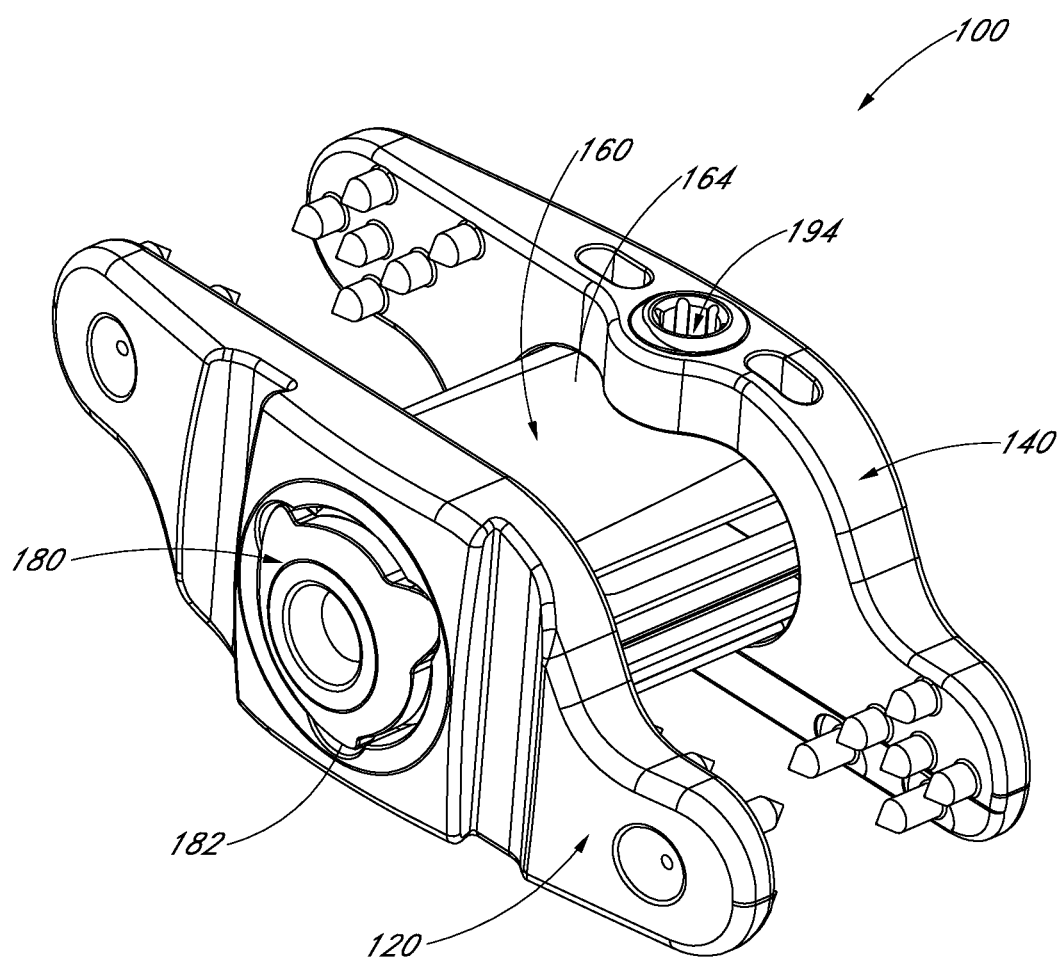
FIG. 2 is a perspective view of the interspinous process device of FIG. 1.
Figure 3:
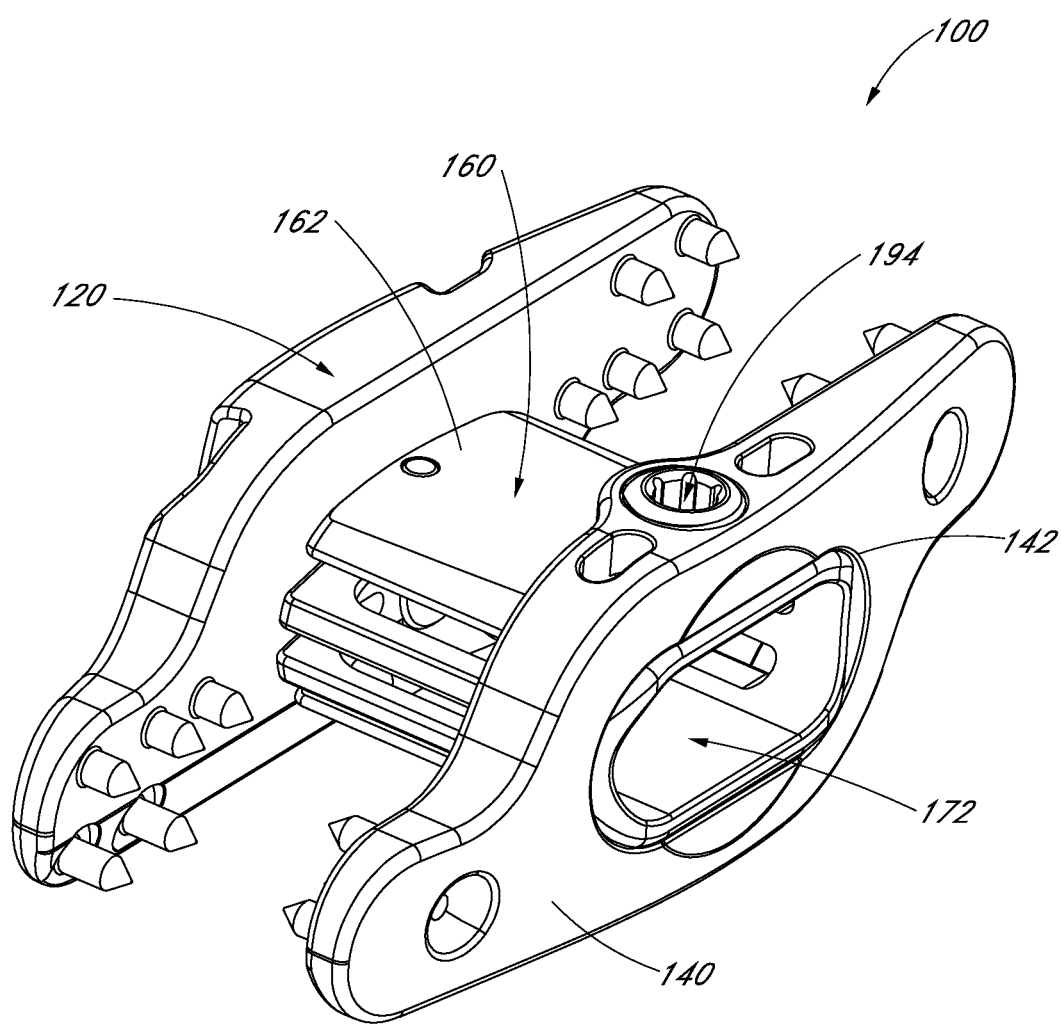
FIG. 3 is another perspective view of the interspinous process device of FIG. 1.

FIGS. 2 and 3 are perspective views of an interspinous process device 100. The first plate 120 and second plate 140 are shown with at least part of the transverse member 160 disposed between the plates. In the illustrated embodiment, the first plate 120 is coupled to the transverse member 160 through a post 180. The post 180 can include a head 182 and a shaft that extends through a hole in the first plate 120. A spring mechanism 190 can be disposed between the post head 182 and the first plate 120 to provide a preload. In some embodiments, the spring mechanism can be positioned at another location or other locations to achieve similar functional preloads, as described further below.

The post 180 can be connected to a first end 162 of the transverse member 160 and the second plate 140 can be connected to a second end 164 of the transverse member 160. The second plate 140 can have an aperture 142 sized and shaped to receive the second end 164 of the transverse member 160. In the illustrated embodiment, the aperture 142 is an oval-shaped through hole that fits the oval cross-sectional shape of the transverse member 160. In other embodiments, the aperture can have any of a plurality of different shapes corresponding to the cross-sectional shape of the transverse member. A fastener 194 can secure the second plate 140 to the transverse member 160. The fastener is illustrated as a setscrew with a hexagonal drive, but in other embodiments can be any functional coupler, such as for example a threaded screw, a clamp, a pin, ratcheting teeth, ball and detent, etc.

Figure 4:
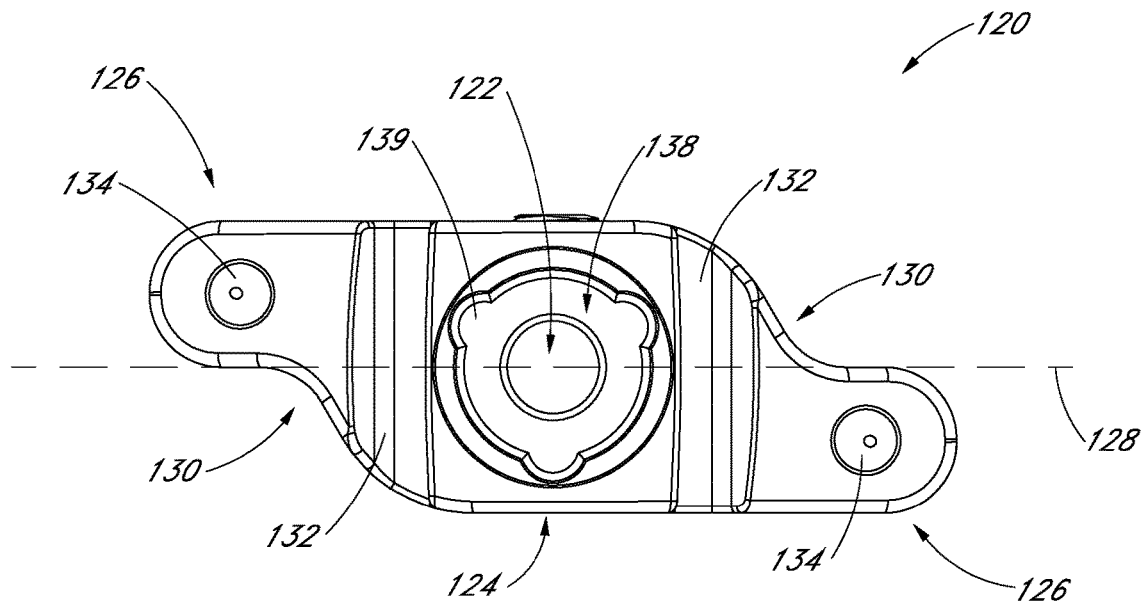
FIG. 4 is a side view of a first plate of the interspinous process device of FIG. 1.

FIG. 4 illustrates a side view of the first plate 120. In the illustrated embodiment, the first plate 120 has an elongate shape comprising a center portion 124 and two arms 126 extending from the center portion 124. The center portion 124 can have a passage 122 configured to pass the post 180 through it. The passage 122 is illustrated as a round through hole, but in other embodiments can be any shaped hole that allows the post 180 to pass through. In some embodiments, the center portion 124 has a cavity 138 that can be configured to accept the head 182 of the post 180. The cavity 138 can be sized and shaped to be complementary to the size and shape of the head 182. The cavity can have anti-rotational features 139 that help prevent the post 180 from rotating in the passage 122. The anti-rotational feature 139 can be a cutout in the cavity 138 that couples with protrusions 186 on the head 182 to stop the post 180 from rotating when the head 182 is situated in the cavity 138. The illustrated embodiment shows three anti-rotational features 139 configured to couple with three protrusions 186 on the head 182. In other embodiments, there can be more or less than three anti-rotational features configured to couple with more or less than three protrusions.

The arms 126 can be offset to a side of the longitudinal axis 128 of the first plate 120 such that the first plate 120 has voids 130 to accommodate the spinal anatomy when implanted. For example, the voids 130 allow the arms 126 to fit around the laminae and/or articular processes of the spine without having to, or at least minimizing, trimming of the patient's spinal anatomy. The first plate 120 can also have depressions 134 on the arms 126 that are configured to receive protrusions on an implant tool. The depressions 134 help stabilize the implant tool on the device 100 while compressing the interspinous process device 100 onto the spinous processes.

Figure 6:
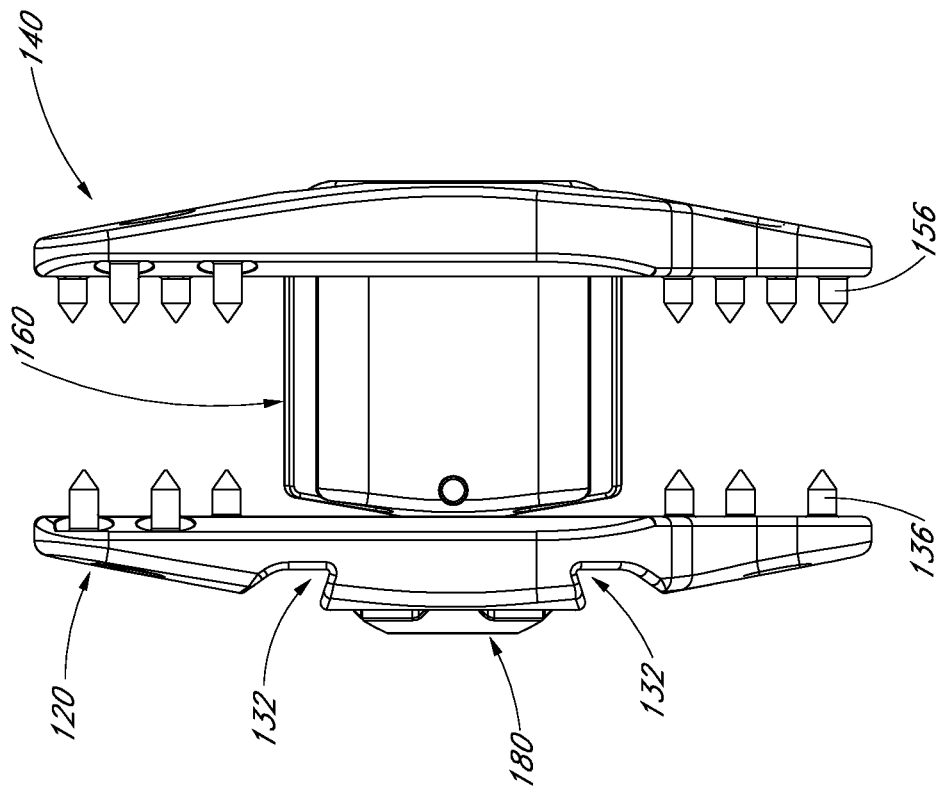
FIG. 6 is a top view of the interspinous process device of FIG. 1.
Figure 7:
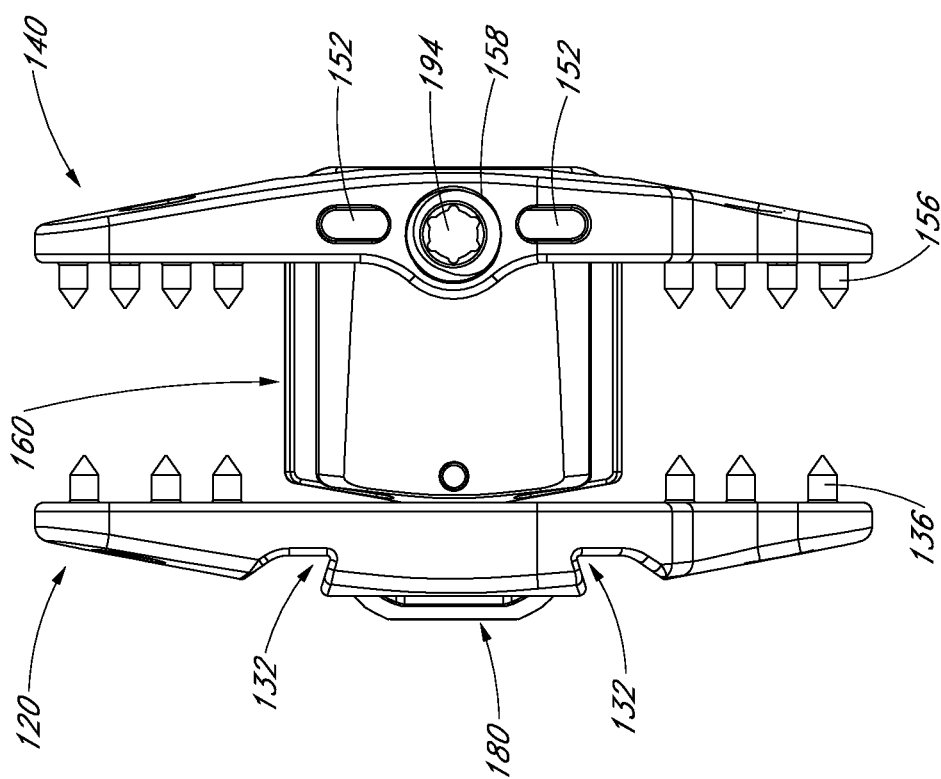
FIG. 7 is a bottom view of the interspinous process device of FIG. 1.

The first plate 120 can have a tool engagement feature 132 for attaching an implant tool. In the illustrated embodiment, the tool engagement feature 132 is two elongate cutouts having a hook or undercut on the inner sides of the cutouts, as best illustrated in FIGS. 6 and 7. The undercut enables the implant tool to engage and hold the first plate 120 while providing a pushing force onto the post 180 to provide the preload onto the device during implantation.

Figure 5:
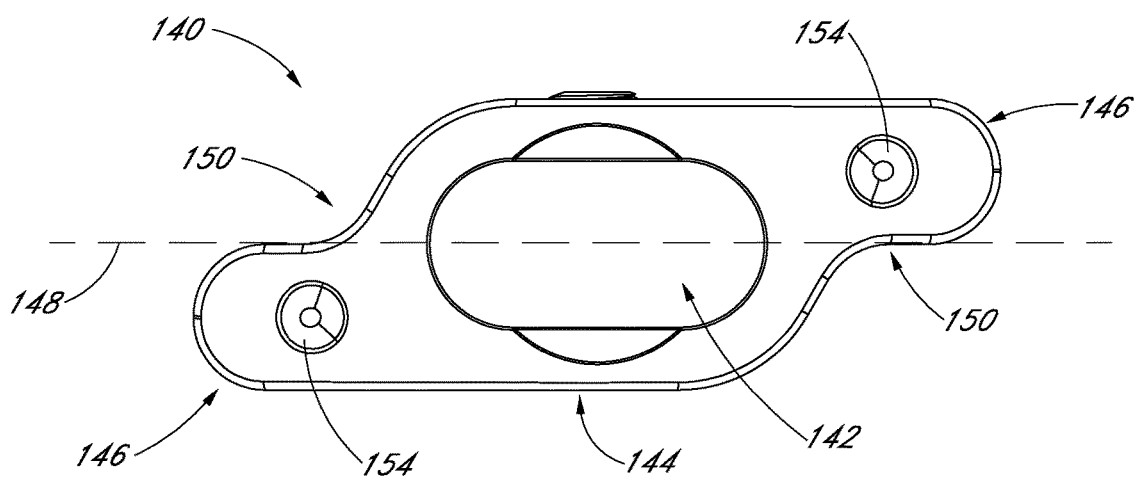
FIG. 5 is a side view of a second plate of the interspinous process device of FIG. 1.

With reference to FIG. 5, the second plate 140 can have the same general shape as the first plate 120. The second plate 140 can have an elongate shape comprising a center portion 144 and two arms 146 extending from the center portion 144. As described above, the center portion 144 can have an aperture 142 for receiving the transverse member 160. In the illustrated embodiment, the aperture 142 is an oval-shaped through hole that matches the oval cross-sectional shape of the transverse member 160. In other embodiments, the aperture can have any shape corresponding to the cross-sectional shape of the transverse member. In some embodiments, the size of the aperture 142 can be slightly larger than the perimeter of the transverse member 160 so that the second plate 140 is able to have an angular adjustment with respect to the transverse member, as described further below. In some embodiments, only certain dimensions of the aperture can be slightly larger to allow angular adjustability in desired directions. For example, in the oval aperture illustrated in FIG. 5, the rounded sides of the oval can be slightly larger while the straight sides have a close fit with the transverse member to allow angular adjustability in a desired direction. In some embodiments, the aperture can be oversized 0.5 mm on the sides compared to the transverse member.

The arms 146 can be offset to a side of the longitudinal axis 148 of the second plate 140 such that the second plate 140 has voids 150 to accommodate the spinal anatomy when implanted, as described above. The second plate 140 can also have depressions 154 on the arms 146 that are configured to receive protrusions on an implant tool. The depressions 154 help stabilize the implant tool on the device 100 while compressing the interspinous process device 100 onto the spinous processes.

With reference to FIG. 6, the second plate 140 can include a tool engagement feature 152. In the illustrated embodiment, the tool engagement feature 152 is located on a top surface of the second plate 140 and includes two oval cavities configured to couple with a tool. For example, two fingers of a tool can be inserted into the tool engagement features 152 and the fingers can be clamped together to hold the second plate 140. In some embodiments, the cavities have an undercut at the bottom of the tool engagement features 152 for accepting hooks on the fingers that help the tool to secure onto the second plate 140.

A fastener 194 can secure the second plate 140 to the transverse member 160. With continued reference to FIG. 6, the fastener 194 is illustrated as a setscrew with a hexagonal drive, but in other embodiments can be any functional coupler, such as for example a threaded screw, a clamp, a pin, ratcheting teeth, ball and detent, etc. In the illustrated embodiment, the second plate 140 has a fastener hole 158 on the top surface that can be threaded to engage the threads on the fastener 194. Once the second plate 140 is in the desired position on the transverse member 160, the fastener 194 can be tightened until it contacts the transverse member 160 to secure the second plate 140 with the transverse member 160. In some embodiments, the second plate 140 can pivot about the fastener 194, even after the fastener 194 is tightened, to allow for angular adjustment when attached to the spinous processes. For example, the aperture 142 of the second plate 140 can be slightly larger than the cross-sectional size of the transverse member 160, allowing the second plate 140 to pivot about the fastener 194.

The second plate 140 can have a general shape that is a mirror of the first plate 120 such that the arms 126 of the first plate 120 are aligned with the arms 146 of the second plate 140, as shown in FIGS. 2 and 3. Accordingly, the arms 126, 146 can be positioned on both sides of the spinous processes at the same locations and can sandwich the processes to provide compressive forces. The first and second plates 120, 140 can have shapes other than those described above, such as rectangular, oval, trapezoidal, polygonal, etc.

With reference to FIGS. 6 and 7, the first plate 120 can have spikes 136 protruding from its inner surface and the second plate 140 can have spikes 156 protruding from its inner surface. When the device 100 is compressed onto the spinous processes 102, 104, the spikes 136, 156 can engage and/or pierce the surface of the spinous processes to secure into place. The spike pattern on each plate can be a mirrored pattern of each other or can be configured such that the spikes are not aligned. The non-aligned configuration may be beneficial in preventing the spikes from puncturing through the processes, which can weaken the structural integrity of the processes. In some embodiments, the first and second plates 120, 140 can have other securement features to engage the spinous processes, such as ridges, hooks, roughened surfaces, and the like.

Figure 8:
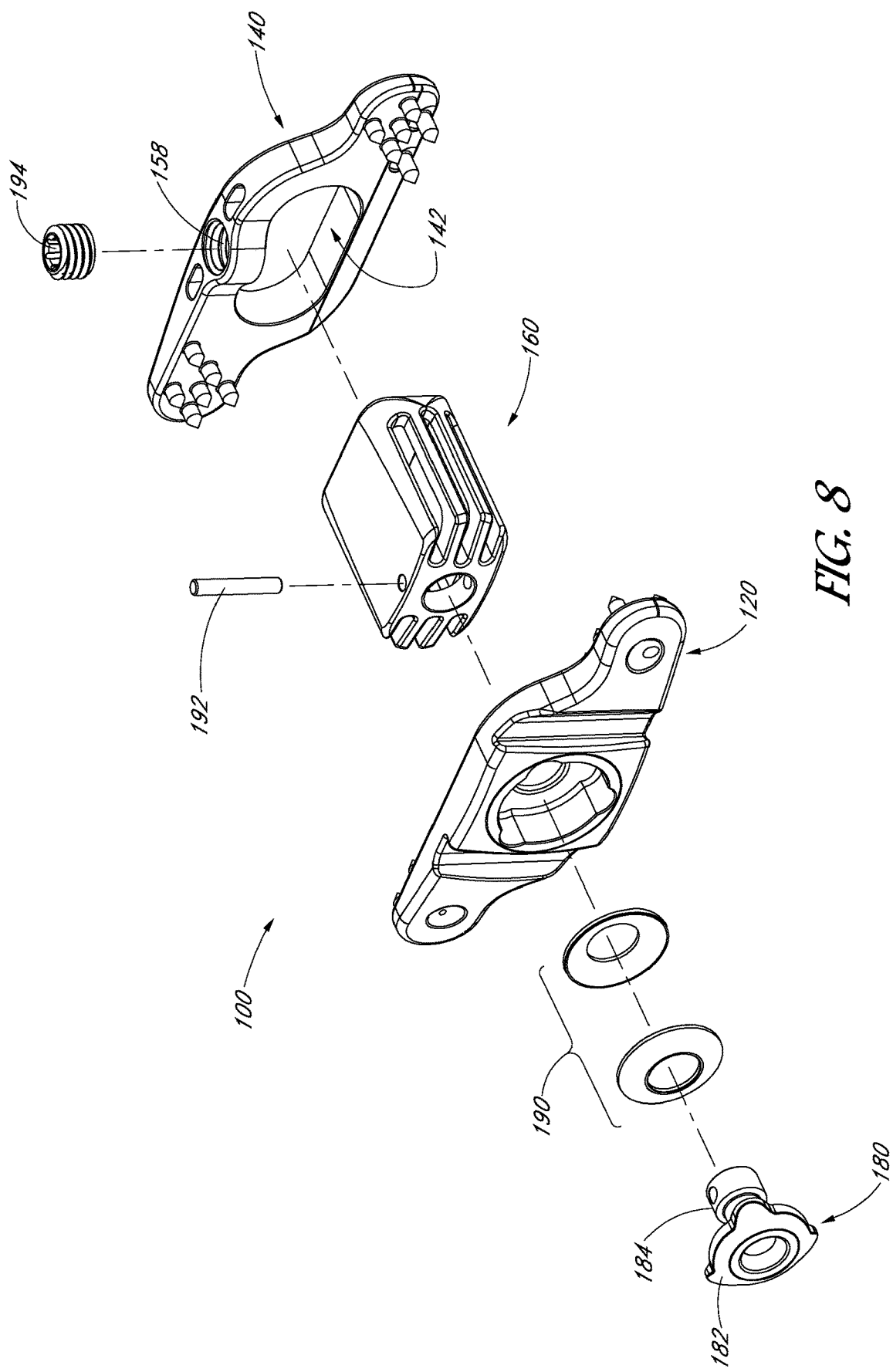
FIG. 8 is an exploded perspective view of the interspinous process device of FIG. 1.

FIG. 8 illustrates an exploded view of an embodiment of the interspinous process device 100. As illustrated, the shaft 184 of the post 180 can be inserted through the passage 122 of the first plate 120. A spring mechanism 190 can be interposed between the cavity 138 of the first plate 120 and the head 182 of the post 180. The spring mechanism can be located at other positions on the device 100 to provide a functional preload, such as on the outer side of the second plate 140 to provide a preload force against the second plate 140. In some embodiments, the spring mechanism can be positioned adjacent either or both sides of the transverse member. In some embodiments, the device 100 can have more than one spring mechanism. For example, spring mechanisms can be positioned adjacent to each plate. In another example, spring mechanisms can be placed next to each of the arms of the plates so that the preload forces can be applied directly to the spikes.

In the illustrated embodiment, the spring mechanism 190 is shown as two opposing beveled washers that can be compressed to store potential spring energy. In other embodiments, the spring mechanism can be other types of springs, such as helical compression springs, wavy washers, and the like. In some embodiments, a resilient material can be used that provides a spring force when compressed, such as for example rubber, composites, plastics, etc.

Figure 9:
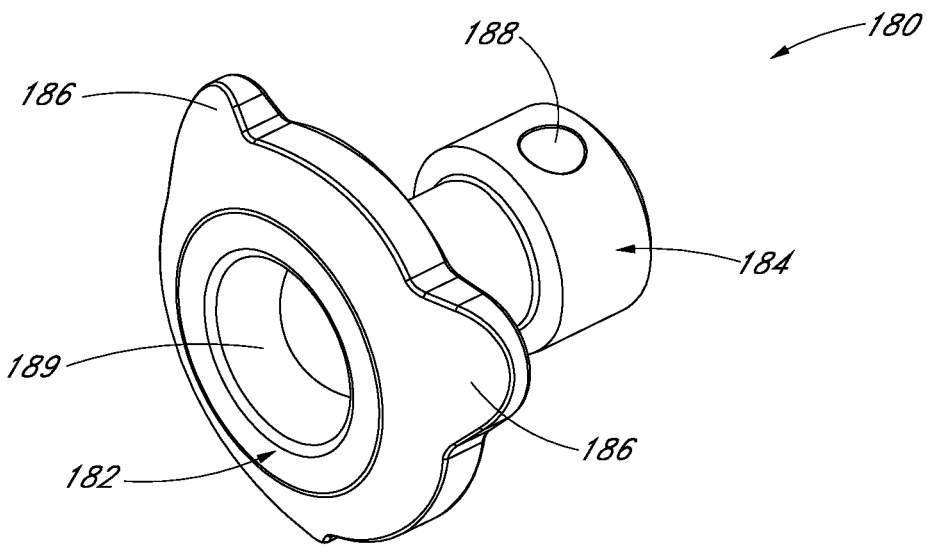
FIG. 9 is a perspective view of a post, which is component of the interspinous process device of FIG. 1.
Figure 10:
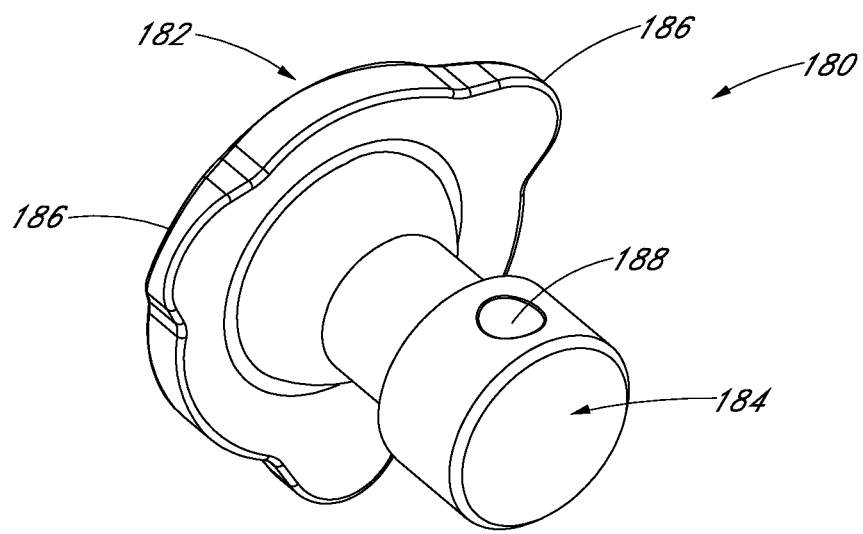
FIG. 10 is another perspective view of the post of FIG. 9.

With reference to FIGS. 9 and 10, close-up views of the post 180 are shown. The post 180 includes a head 182 and a shaft 184 extending from the head 182. The shaft 184 is sized to fit through the passage 122 of the first plate 120, while the head has a larger cross-section such that it cannot fit through the passage 122. The head 182 can be shaped to fit into the cavity 138 of the first plate 120 and can include protrusions 186 to help prevent the post 180 from spinning relative to the first plate 120, as discussed above. The head 182 can include a depression for engagement with a tool, as discussed further below. In some embodiments the head 182 can include a protrusion that engages with a depression on the tool. The shaft 184 can have a hole 188 extending through it used for coupling with the transverse member 160.

Figure 11:
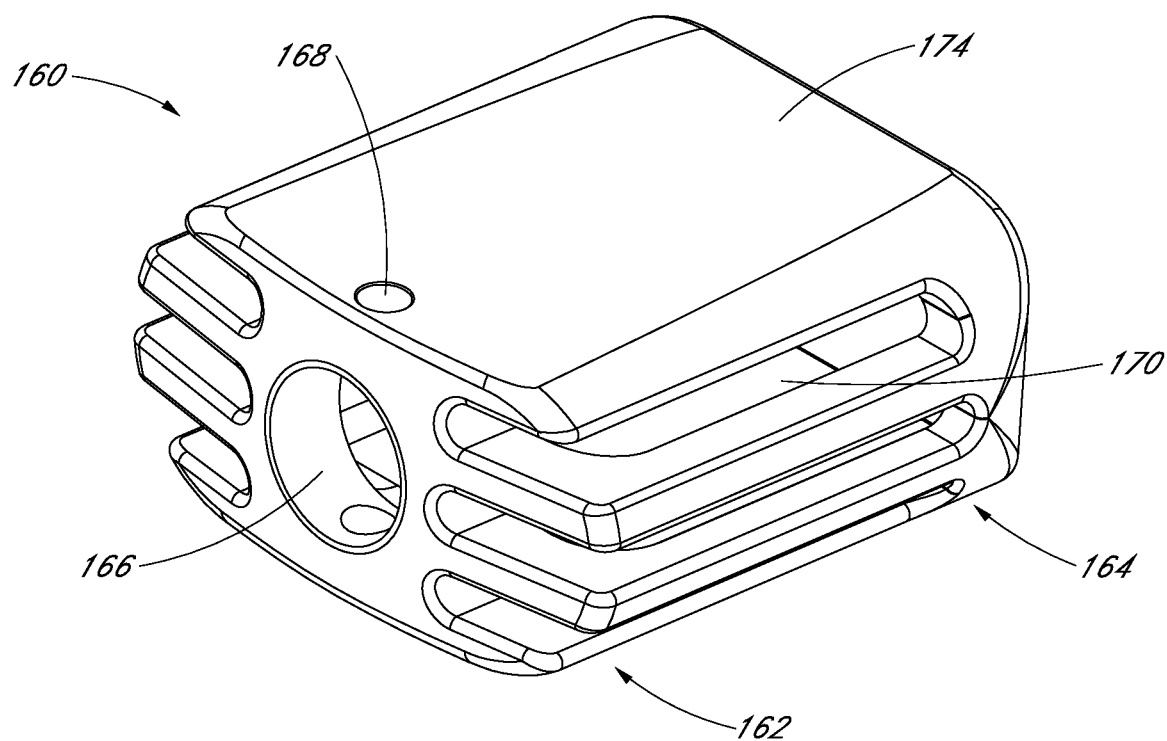
FIG. 11 is a perspective view of a transverse member, which is component of the interspinous process device of FIG. 1.

With continued reference to FIG. 8, after the shaft 184 of the post 180 is inserted through the passage 122 of the first plate 120, the shaft 184 can be attached to the transverse member 160. As illustrated in FIG. 11, the transverse member 160 can have a socket 166 at the first end 162 to accept the shaft 184 of the post 180. The first end 162 can have a hole 168 that extends at least partially through the width of the transverse member 160 and through the socket 166. When the shaft 184 is inserted into the socket 166, the hole 188 in the shaft 184 can align with the hole 168 in the transverse member 160. A pin 192, or other functional fastener, can be inserted into the holes 168 and 188 to attach the post 180 to the transverse member 160. Examples of other functional fasteners can include a threaded connection, press-fit, swage, or weld between the post and transverse member. In some embodiments, the post and transverse member are made of a single integral piece.

In some embodiments, when the first plate 120, post 180, spring mechanism 190 and transverse member 160 are assembled together, the first plate 120 is not directly connected to the transverse member 160. The first plate 120 is connected to the post 180, which in turn is connected to the transverse member 160. In some configurations, the first plate 120 does not contact the transverse member 160.

Figure 12:
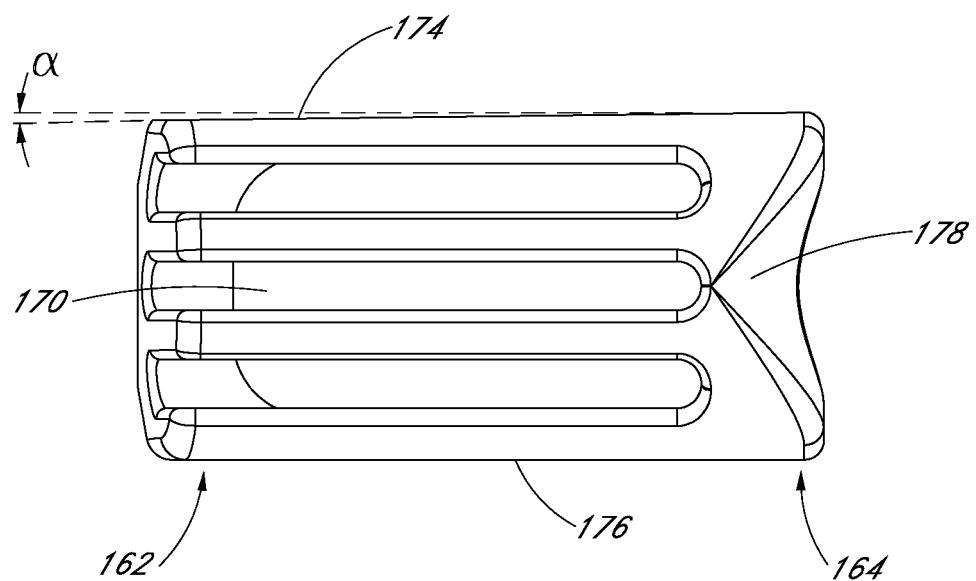
FIG. 12 is a side view of the transverse member of FIG. 11.

With reference to FIGS. 11 and 12, the transverse member 160 can have a generally rectangular cuboid shape. In other embodiments, the transverse member 160 can have other functional shapes, such as a cube, ball, C-shaped frame, wavy strip, etc. The socket 166 and hole 168 can be disposed at the first end 162 and an orifice 172 can be disposed on the second end 164. The orifice 172 can be best seen in FIG. 3. The orifice 172 provides access to a chamber in the transverse member 160 configured to hold material to assist bone growth, such as autograft, allograft, demineralized bone matrix (DBM), synthetic ceramics and the like. The second end 164 can have one or more edges 178 that are chamfered to help insertion of the transverse member 160 through the aperture 142. The chamfered edges 178 can also provide clearance for the second plate 140 to pivot on the transverse member 160. The transverse member 160 can have openings 170 that provide access from the outer surface of the transverse member 160 to the chamber. The openings 170 are illustrated as slots in the side wall of the transverse member 160. The slots are shown extending from the side wall to the first end wall of the transverse member 160. In some embodiments, the openings 170 are round holes in the walls of the transverse member 160. The openings 170 help provide access to the bone graft in the chamber for improved bone ingrowth and integration of the device 100 with the native anatomy.

With reference to FIG. 12, the transverse member 160 can have a first surface 174 and a second surface 176 on the opposite side of the transverse member 160 from the first surface 174. In some embodiments, the first surface 174 is substantially parallel with the second surface 176. In other embodiments, the first surface 174 of the transverse member 160 is angled such that the thickness of the transverse member 160 at the first end 162 is less than the thickness of the transverse member 160 at the second end 164. In the illustrated embodiment, the first surface 174 has an angle α from the horizontal plane. The angle α can be at least approximately 0.1 degree and/or less than or equal to approximately 7 degrees. In some embodiments, the angle α can be at least approximately 0.1 degree and/or less than or equal to approximately 3 degrees. In some embodiments, the angle α is approximately 0.7 degree. The angle α helps to maintain the second plate 140 on the transverse member 160. The fastener 194 on the second plate 140 is tightened on the transverse member 160 and the angle α helps prevent the second plate 140 from moving toward the second end 164, which can cause loosening of the device 100 from the spinous processes.

With continued reference to FIG. 8, the second plate 140 can be coupled to the transverse member 160 by inserting the transverse member 160 into the aperture 142. When the desired position of the second plate 140 along the transverse member 160 is achieved, the fastener 194 can be inserted into the fastener hole 158 and tightened until the fastener 194 engages the transverse member 160 to fix the position of the second plate 140. In some embodiments, the second plate 140 is able to pivot about the fastener while attached to the transverse member 160, as discussed above.

Figure 13:
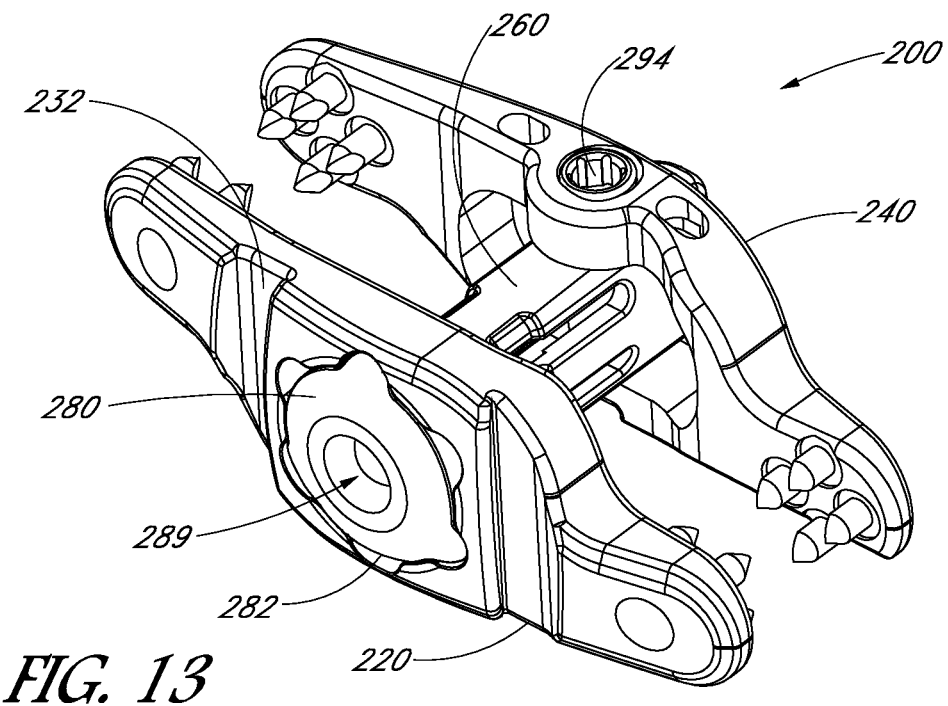
FIG. 13 is a perspective view of an interspinous process device, according to another embodiment of the present disclosure.
Figure 14:
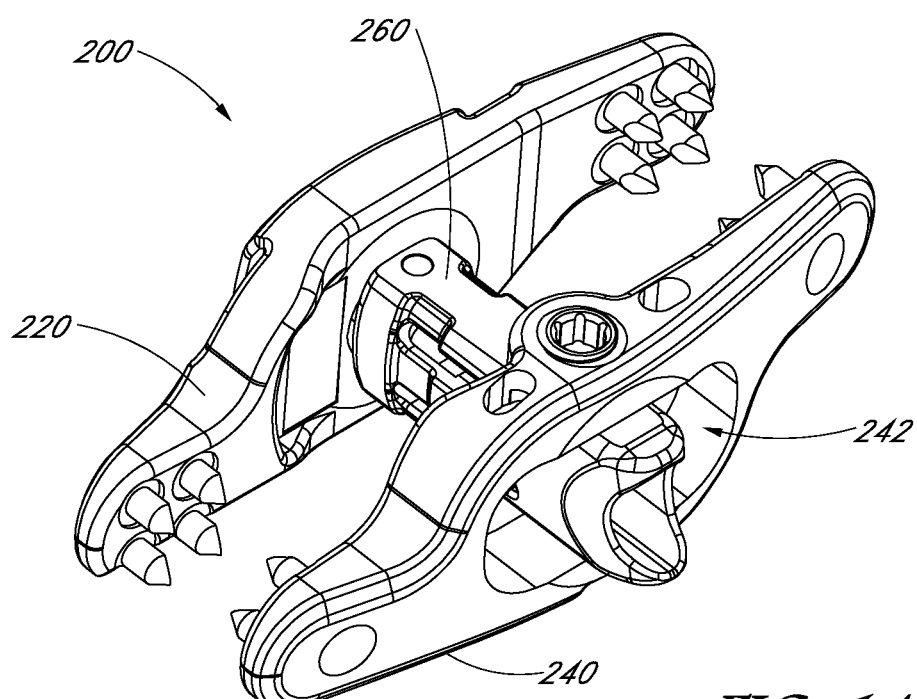
FIG. 14 is another perspective view of the interspinous process device of FIG. 13.

FIGS. 13 and 14 illustrate another embodiment of an interspinous process device 200. The interspinous process device 200 can have one or more components that are similar to other embodiments disclosed herein. The device 200 can comprise a first plate 220 and a second plate 240, which are configured to span from the superior spinous process 102 to the inferior spinous process 104. A transverse member 260 can extend between the first plate 220 and the second plate 240 and can be configured for placement in the interspinous space.

The transverse member 260 can be wide enough to contact the inferior surface of the superior spinous process 102 and the superior surface of the inferior spinous process 104. In some embodiments, the transverse member 260 is wide enough to distract the spinous processes apart to open the intervertebral foramen for treatment of spinal stenosis or other spinal condition. In some embodiments, the transverse member 260 helps maintain the proper spacing between the spinous processes 102, 104. The illustrated embodiment has a transverse member 260 with a width smaller than some other embodiments of the transverse member disclosed herein. A transverse member with a relatively smaller width may be desirable for smaller anatomies (e.g. children) or when large distraction of the vertebrae is undesirable.

With continued reference to FIGS. 13 and 14, a post 280 can couple the first plate 220 to the transverse member 260. The post 280 can include a head 282 and a shaft that extends through a hole in the first plate 220. The head 282 can include a depression 289 or protrusion for engagement with a tool, as discussed above. A spring mechanism (not shown) can be disposed between the post head 282 and the first plate 220 to provide a preload. In some embodiments, the spring mechanism can be positioned at another location or other locations to achieve similar functional preloads, as described above.

The post 280 can be connected to a first end of the transverse member 260 and the second plate 240 can be connected to a second end of the transverse member 260. The second plate 240 can have an aperture 242 configured to receive the second end of the transverse member 260. In the illustrated embodiment, the aperture 242 is an oval-shaped through hole that is sufficiently large for the transverse member 260 to pass through. In other embodiments, the aperture can have any of a plurality of different shapes. In some embodiments, the aperture can have a size and shape corresponding to the cross-sectional shape of the transverse member 260. A fastener 294 can secure the second plate 240 to the transverse member 260. The fastener is illustrated as a setscrew with a hexagonal drive, but in other embodiments can be any functional coupler, such as for example a threaded screw, a clamp, a pin, ratcheting teeth, ball and detent, etc.

One or more components of the interspinous process device 100 can be made of a biocompatible material, such as polyether ether ketone (PEEK), titanium, titanium alloy, cobalt chrome molybdenum alloy, etc. In some embodiments, the components can be made of different materials, such as for example the plates being made of titanium and the transverse member being made of PEEK. In some embodiments, the components that need strength may be made of metallic material, such as the spring mechanism 190, pin 192, and post 180, while the other components can be made of PEEK or other material.

In some embodiments, the device 100 can have a coating to help the device integrate with the surrounding bone. For example, a titanium deposition can be sprayed or otherwise applied to at least some of the surfaces of the device 100. The titanium coating can be porous to help promote bone fusion with the device 100. In some embodiments, only the portions of the device that contact the spinous processes may be coated, such as the transverse member 160 and/or the inner surfaces of the plates 120, 140. Another coating material that can be used to promote fusion is hydroxylapatite.

The interspinous process device 100, 200 can be implanted using an interspinous process (ISP) inserter. The description of the ISP inserter will be described herein in combination with an embodiment of the interspinous process device 200. However, the ISP inserter can be used with other embodiments of the interspinous process device described herein, as well as various alternatives. The ISP inserter can comprise a first inserter component 600, illustrated in FIG. 15, and a second inserter component 700, illustrated in FIG. 18.

Figure 15:
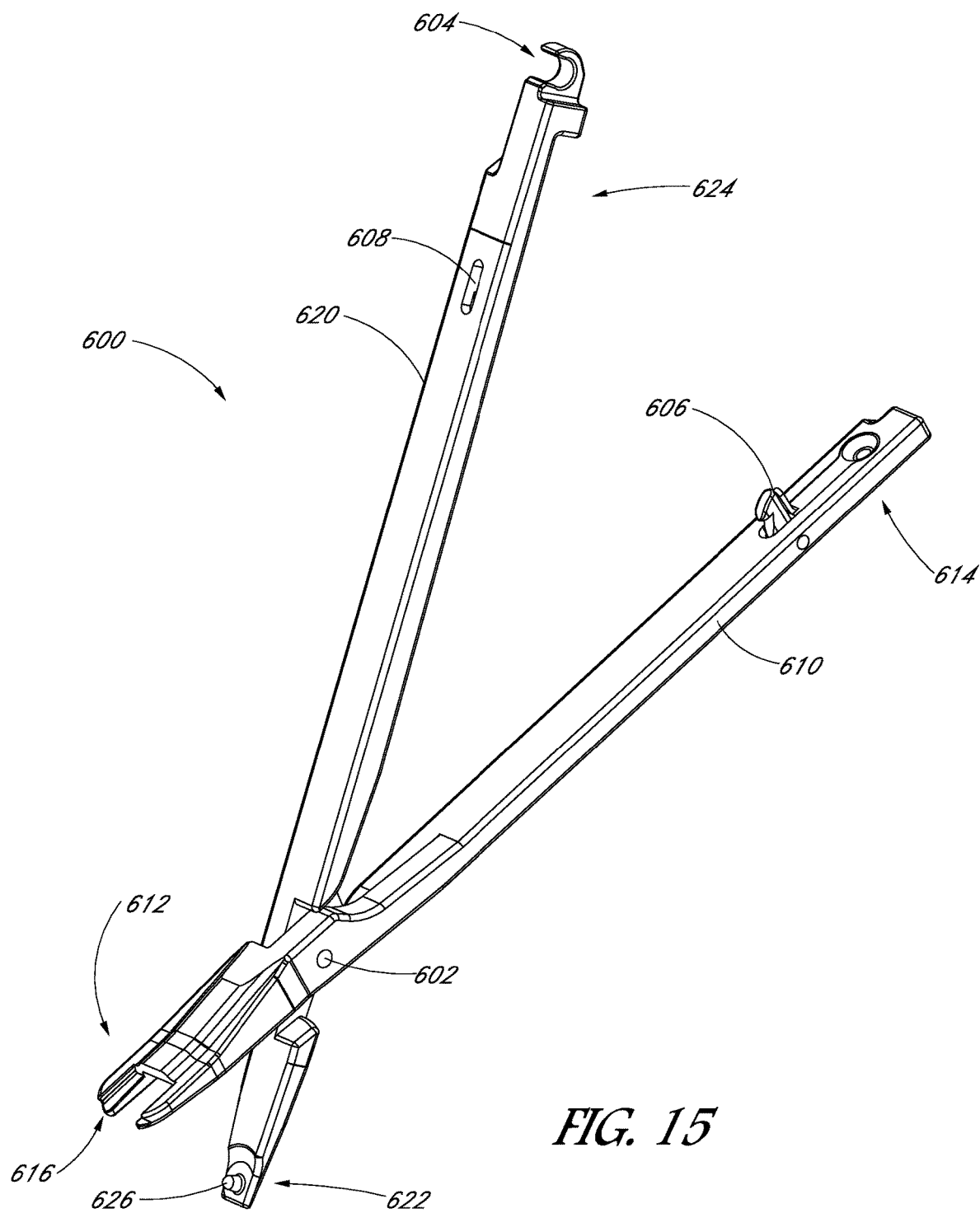
FIG. 15 is a perspective view of a first inserter component for use with an interspinous process device, according to an embodiment of the present disclosure.

With reference to FIG. 15, the first inserter component 600 can comprise a first arm 610 and a second arm 620. The first arm 610 can be an elongate member with a distal portion 612 and a proximal portion 614. The distal portion 612 can be configured to couple with the first plate 220. The proximal portion 614 can be a handle for manipulating the distal portion 612. In some embodiments, the proximal portion 614 has a latch 606 for securing with the second arm 620. The second arm 620 can be an elongate member with a distal portion 622 and a proximal portion 624. The distal portion 622 can be configured to engage the head 282 of the post 280. The proximal portion 624 can be a handle with a latch engagement 608 for coupling with the latch 606 on the first arm 610.

The proximal portion 624 of the second arm 620 can include a first hinge connector 604 that is configured to couple with a complementary second hinge connector on the second inserter component 700. In the illustrated embodiment, the first hinge connector 604 is a hook that is configured to couple with a cylinder on the second hinge connector to form a releasable hinge. In other embodiments, the first hinge connector can have any of a plurality of different releasable hinge designs that are configured to pivotally couple with a complementary second hinge connector on the second inserter component 700, such as a shaft and channel coupling, a ball and socket, and the like. In some embodiments, the first hinge connector 604 can be on disposed on the proximal portion 614 of the first arm 610 instead of, or in addition to, the second arm 620.

The first arm 610 and second arm 620 can be hingedly connected at a pivot 602. In the illustrated embodiment, the pivot 602 is positioned adjacent the distal portions 612, 622 of the first and second arms 610, 620. Positioning the pivot 602 at or near the distal portions 612, 622 can advantageously aid the user to attain leverage with the handles of the first and second arms 610, 620 to apply the preload to the interspinous process device 100, 200, as discussed in further detail below. In some embodiments, the pivot 602 can be at any position along the length of the first and second arms 610, 620. For example, the pivot 602 can be near the midpoint of the first and second arms 610, 620 or adjacent the proximal portions 614, 624 of the first and second arms 610, 620. The pivot 602 can be any functional hinge, such as a pin coupled in a hole, or a ball and socket hinge.

The latch 606 can be disposed on the first arm 610 and configured to releasably couple with the latch engagement 608 on the second arm 620. In some embodiments, the latch 606 is on the second arm 620 and the latch engagement 608 is on the first arm 610. In the illustrated embodiment the latch 606 is a hook that is biased in the closed direction and the latch engagement 608 is an opening configured to receive the hook. The hook has an angled surface that contacts an edge of the opening and deflects the hook so that the hook can pass through the opening. The hook can exit the opening and catch the other edge of the opening to hold the first inserter component 600 in a closed configuration. The latch 606 can be biased in the closed direction by a spring, elastic deformation of the hook, or other functional spring force. To release the latch 606, it can be deflected manually to separate the latch 606 from the latch engagement 608. In some embodiments, the latch is released by depressing a release button. In some embodiments, the latch can decouple from the latch engagement by applying a certain amount of separation force, so that the first inserter component 600 is transitioned to an open configuration by pulling apart the first arm 610 from the second arm 620.

Figure 16:
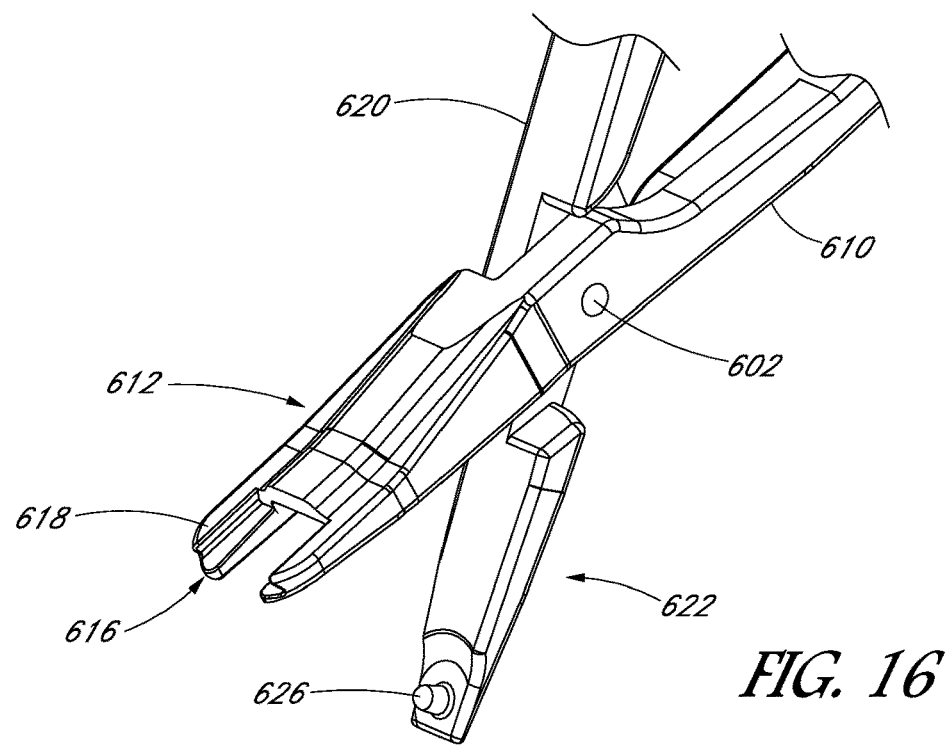
FIG. 16 is a close-up of the distal end of the first inserter component of FIG. 15.

FIG. 16 illustrates a close-up of the distal portions 612, 622 of the first and second arms 610, 620, respectively. The distal portion 612 of the first arm 610 can have a first plate engagement 616 that is configured to couple with the first plate 220. The first plate engagement 616 can have a structure that is complementary to the surface of the first plate 220. In the illustrated embodiment, the first plate engagement 616 has ribs 618 that engage with the tool engagement feature 232 on the first plate 220. The ribs 618 can be undercut with an angled surface to engage the undercut surface on the 232. The undercut enables the first plate engagement to hold the first plate 220 while securing the first plate 220 when the preload is applied to the post. In other embodiments, the first plate engagement can have any functional coupler for releasable coupling with the first plate 220.

The distal portion 622 of the second arm 620 can have a post head engagement 626 that is complementary to a second arm engagement feature 289 on the head 282 of the post 280. When the first inserter component 600 is in a closed configuration, the post head engagement 626 is configured to push against the head 282 toward the first plate 220, which is held fixed by the first plate engagement 616. In the illustrated embodiment, the post head engagement 626 is a rounded protrusion that engages a depression in the head 282. In some embodiments, the post head engagement can be a cavity that engages a protrusion on the head.

Figure 17:
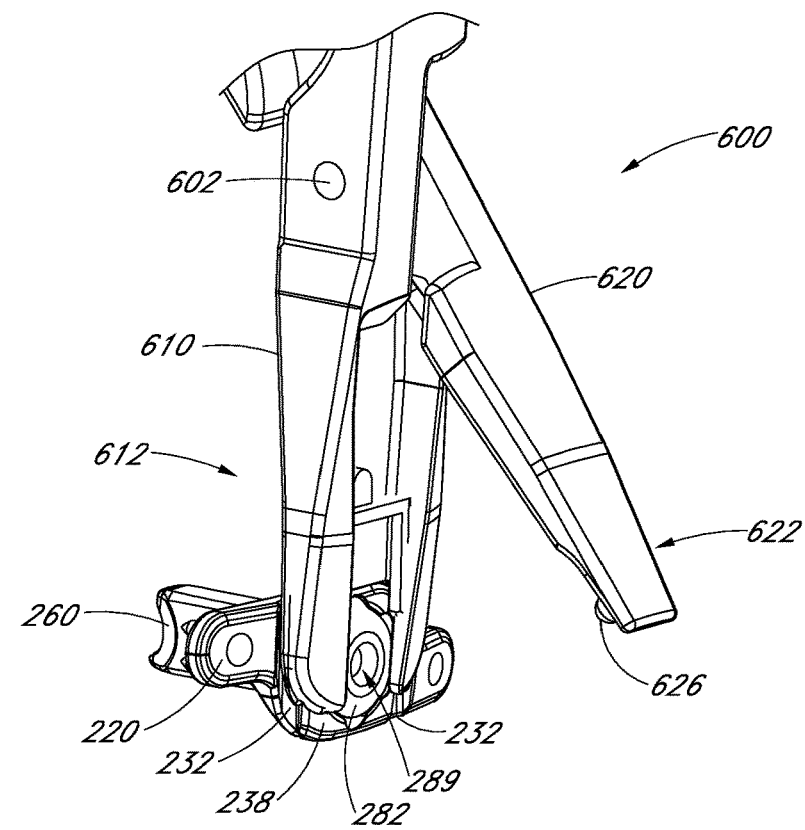
FIG. 17 is another close-up of the distal end of the first inserter component of FIG. 15, coupled to a portion of an interspinous process device.

FIG. 17 illustrates the first inserter component 600 coupled to a first plate 220 with a transverse member 260 and post 280. The ribs 618 on the first arm 610 can engage the tool engagement features 232 on the first plate 220. The post head engagement 626 on the second arm 620 can be aligned with the second arm engagement feature 289 on the head 282 of the post 280 when the first plate 220 is seated on the first plate engagement 616. When the first inserter component 600 is transitioned into the closed configuration, the post head engagement 626 presses the head 282 against the first plate 220 to compress the spring mechanism and apply a preload to the interspinous process device 200. The latch 606 can temporarily lock the first arm 610 with the second arm 620 to help maintain the preload as the interspinous process device 200 is implanted using the first inserter component 600.

Figures 18, 19:
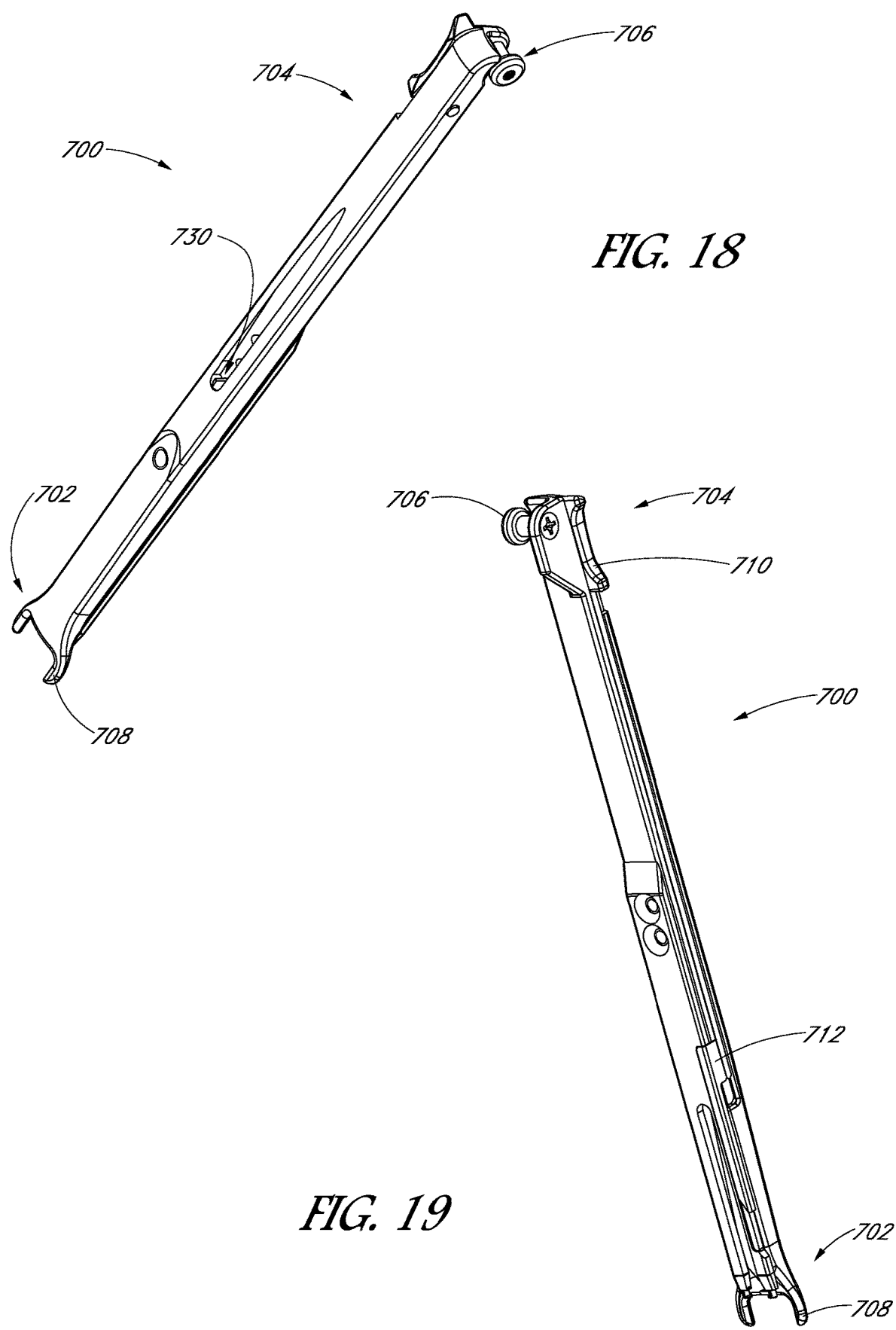
FIG. 18 is a perspective view of a second inserter component for use with an interspinous process device, according to an embodiment of the present disclosure.
FIG. 19 is another perspective view of the second inserter component of FIG. 18.

With reference to FIGS. 18 and 19, the second inserter component 700 can be an elongate member with a distal portion 702 and a proximal portion 704. The distal portion 702 can be configured to couple with the second plate 240. The proximal portion 704 can be a handle for manipulating the distal portion 702 during surgery. In some embodiments, the proximal portion 704 has a second hinge connector 706 for securing with the first inserter component 600.

The second hinge connector 706 is configured to couple with the complementary first hinge connector 604 on the first inserter component 600. In the illustrated embodiment, the second hinge connector 706 is a shaft with a diameter that is configured to releasably couple with the hook on the first hinge connector 604 to form a hinge. In other embodiments, the second hinge connector can have any of a plurality of different releasable hinge designs that are configured to pivotally couple with a complementary first hinge connector on the first inserter component 600, such as a shaft and channel coupling, a ball and socket, and the like.

The distal portion 702 of the second inserter component 700 can have a second plate engagement 708 that is configured to couple with and support the second plate 240 of the interspinous process device 200. The second plate engagement 708 can have a C-shape that is configured to support the sides of the second plate 240 during implant insertion, while not obstructing the aperture 242. In some embodiments, the second plate engagement 708 can hold the second plate 240, such as with hooks, magnets, clamps, and the like.

Figure 20:
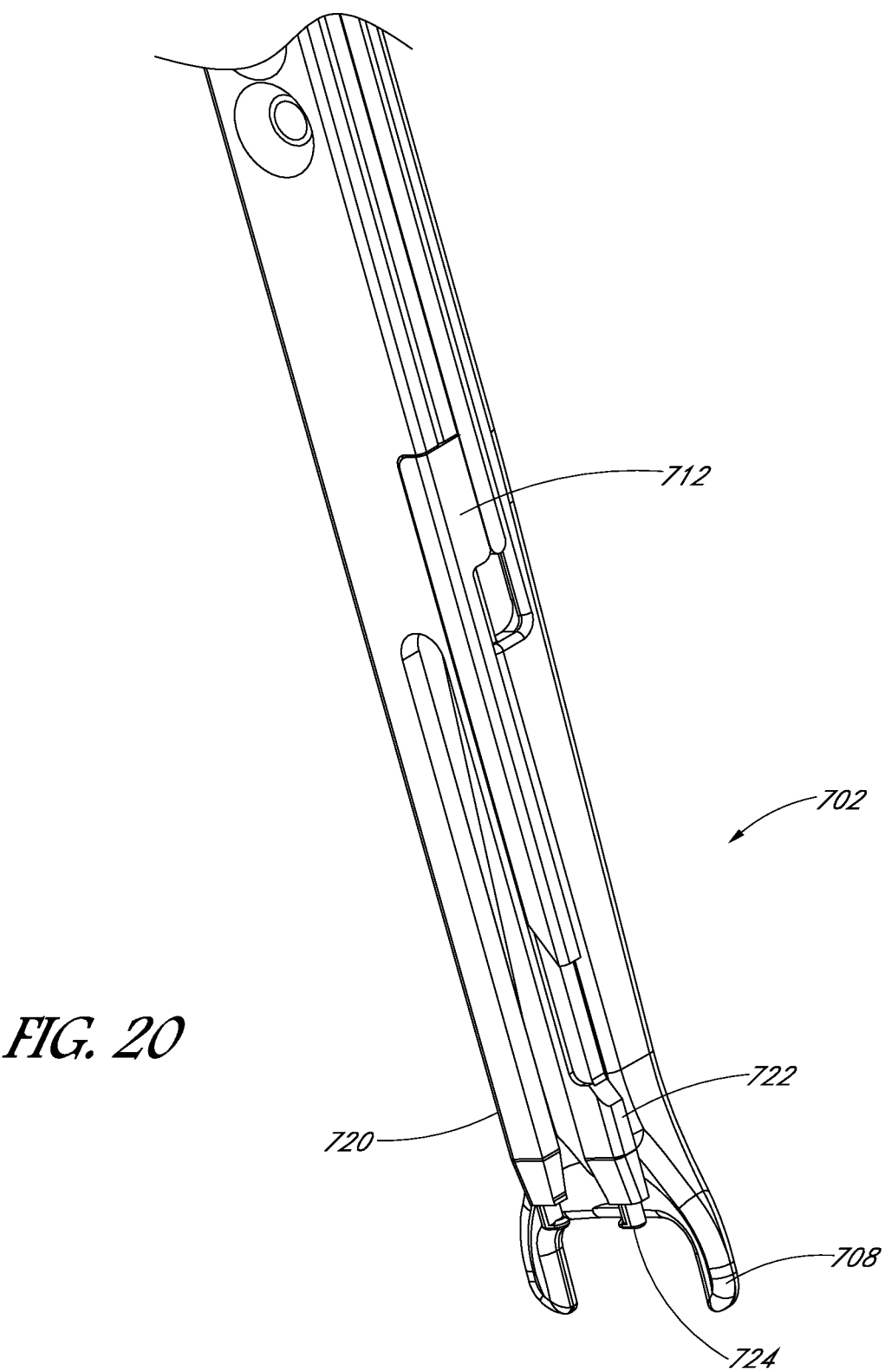
FIG. 20 is a close-up perspective view of the distal end of the second inserter component of FIG. 18.
Figure 21:
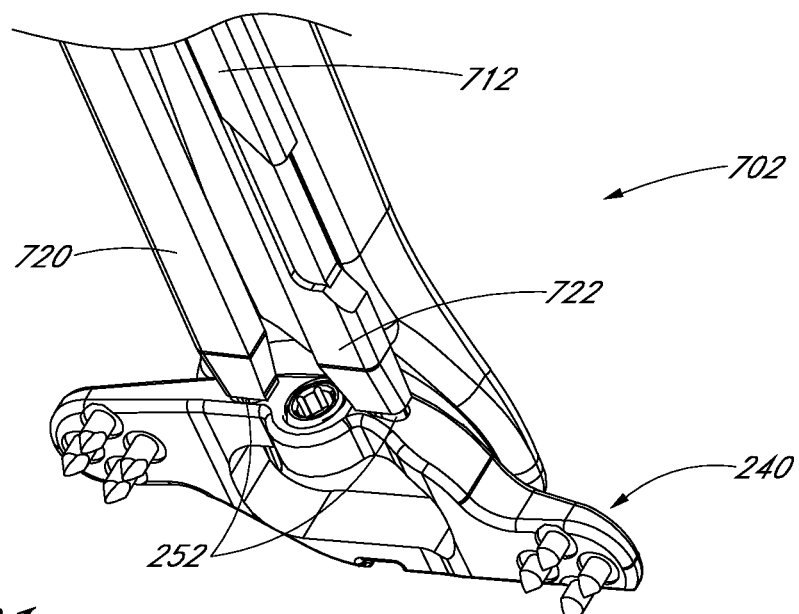
FIG. 21 is another close-up perspective view of the distal end of the second inserter component of FIG. 18, coupled to a portion of an interspinous process device.

With reference to FIGS. 20-21, the second inserter component 700 can include a first finger 720 and a second finger 722 that are configured to hold the second plate 240. The first and second fingers 720, 722 can be elongate extensions with engagement tips 724 that are configured to couple with tool engagement features 252 on the second plate 240. In the illustrated embodiment, the engagement tips 724 are hooks that are inserted into the cavities of the tool engagement features 252. The hooks can engage undercuts in the tool engagement feature 252 to secure the second plate 240 with the second inserter component 700. In other embodiments, the second plate 240 can be held by other mechanisms, such as clamps, magnets, fasteners, or other functional coupler.

In some embodiments, one or more of the first finger 720 and the second finger 722 are connected to an actuation lever 712. The actuation lever 712 can be an elongate shaft that extends along the longitudinal length of the second inserter component 700. An actuator 710 can be disposed on the proximal portion 704 of the second plate 240, which activates the actuation lever 712. The actuation lever 712 can move the first finger 720 and/or the second finger 722 from a release configuration to an engagement configuration with the tool engagement features 252. For example, the illustrated embodiment shows the actuation lever 712 disposed along the second finger 722.

When the actuation lever 712 is moved distally, it acts upon the second finger 722 to push the second finger 722 laterally toward the first finger 720. The second finger 722 can have a hinge or can be cantilevered so that the second finger 722 can deflect toward the first finger 720. The first finger 720 and second finger 722 can be clamped together in the tool engagement feature 252 such that the engagement tips 724 interlock with the undercuts and the second plate 240 is secured to the second inserter component 700. When the actuation lever 712 is moved in the proximal direction, the second finger 722 can separate from the first finger 720 wherein the engagement tips 724 are unobstructed by the undercuts and the second plate 240 is released from the second inserter component 700.

Figure 22:
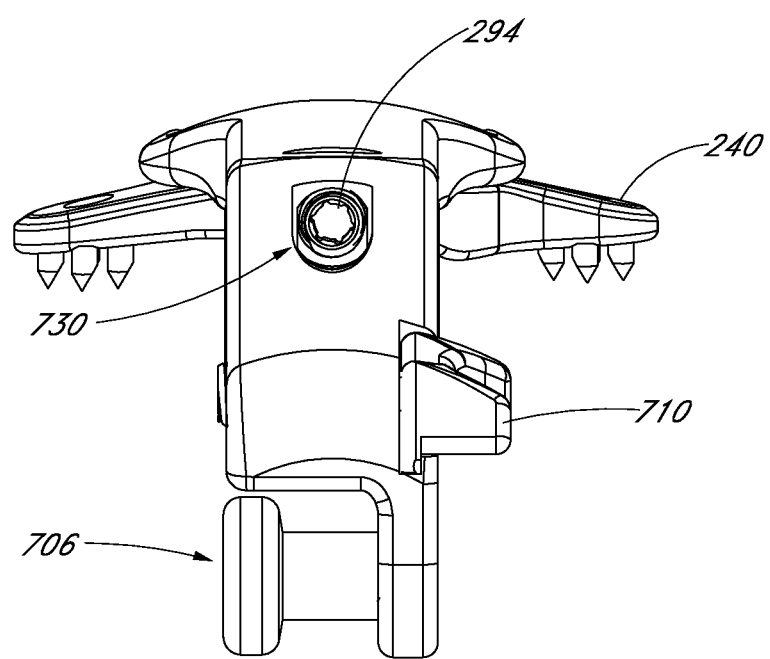
FIG. 22 is a view from the proximal end of the second inserter component of FIG. 18, showing the access channel.
Figure 29:
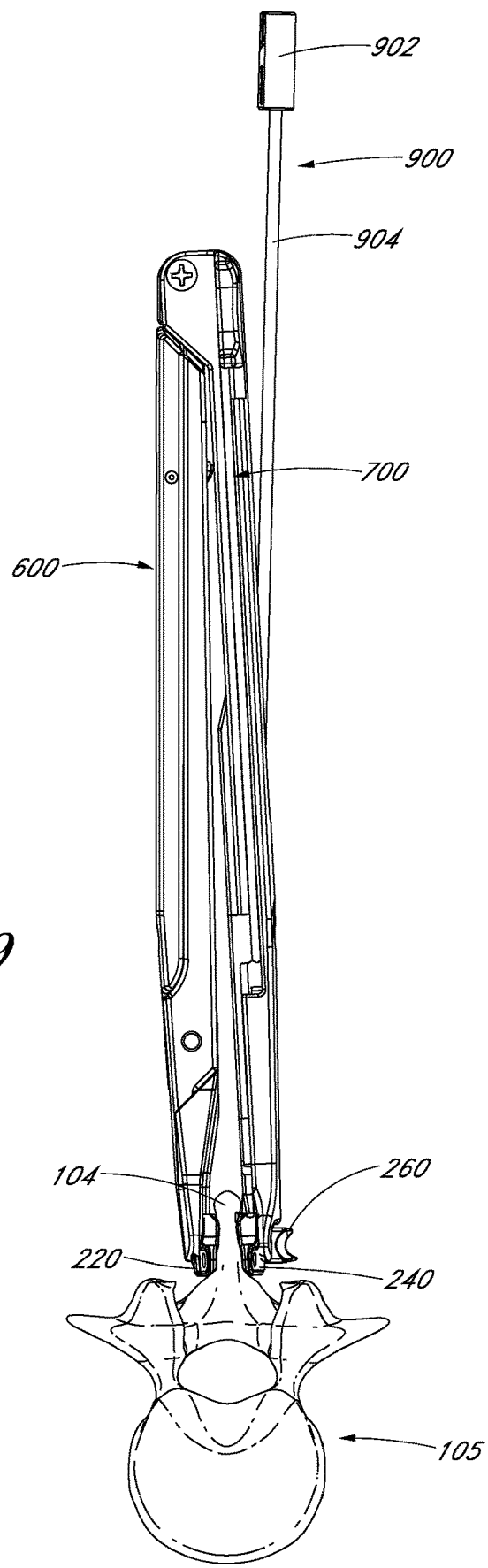
FIG. 29 illustrates the inserter device of FIG. 26 and a driver tool extending through the inserter device and coupled to the second portion of the interspinous process device.

FIG. 22 illustrates a proximal view the second inserter component 700 along a longitudinal length of an access channel 730. With reference to FIG. 18, the access channel 730 is a passage from toward the proximal portion 704 to the distal portion 702 of the second inserter component 700, configured to provide access for an elongate driver tool to reach the fastener 294 on the second plate 240. After the second plate 240 is coupled with the transverse member 260 at the implant site, the fastener 294 can be accessed from outside the surgical incision by inserting the elongate driver tool through the access channel of the second inserter component 700 to secure the interspinous process device 200 to the spinous processes, as illustrated in FIG. 29.

In some embodiments, the second inserter component 700 can have a prepositioned shaft that engages the fastener 294 when the second plate 240 is coupled with the second inserter component. The shaft can be engaged from the proximal portion 704 to actuate the shaft, which in turn actuates the fastener 294. In other embodiments, the fastener 294 can be actuated from the proximal portion 704 through other methods, such as using interlocking gears, self-powered drivers, and the like.

The interspinous process (ISP) inserter can be used to implant the interspinous process device. The methods of using the ISP inserter can be employed to implant any embodiment of the interspinous process device described herein. Any reference made to a specific embodiment of the interspinous process device in the description of the methods can apply to other embodiments of the interspinous process device.

In some methods of using the interspinous process device 100, 200, the device can be implanted through an open surgical procedure or a minimally invasive procedure. The device 100, 200 can be implanted from a posterior, posterolateral, or a lateral approach. The device 100, 200 can be partially assembled or fully assembled before delivery to the implant site, or the device 100, 200 can be assembled in situ at the implant site.

After the vertebrae are identified for treatment, the implant site can be prepared prior to introduction of the spinous process device 100, 200. The interspinous ligament between the spinous processes can be cut and/or removed to make space for the device 100, 200. In some situations, the spinous process device can be implanted without cutting or removing the interspinous ligament. Also, depending on the procedure, the supraspinous ligament can be cut and/or removed. The surfaces of the spinous processes that are to contact the device 100, 200 can be roughened or otherwise prepared to help fusion with the device 100, 200. In some situations, the spinous processes can be distracted using a known distractor tool and procedure.

In some embodiments, the first plate 120, 220, transverse member 160, 260, post 180, 280 and spring mechanism 190 are preassembled prior to being inserted into the patient. One or more of the orifice 172, openings 170 and the outer surfaces of the transverse member 160, 260 can have bone growth material, such as allograft or DBM. The assembly can be coupled to the first inserter component 600 by engaging the first plate engagement 616 with the tool engagement features 132, 232 on the first plate 120, 220. As described above, the first inserter component 600 can be a plier-like tool with a forked first arm 610 configured to engage the tool engagement features 132, 232 and the second arm 620 configured to engage the depression 189 or protrusion on the post 180, 280. The first inserter component 600 can be actuated to apply a preload on the spring mechanism 190. In some embodiments, the first inserter component 600 can be held in the actuated (i.e. closed) configuration by a latch 606.

Figure 23:
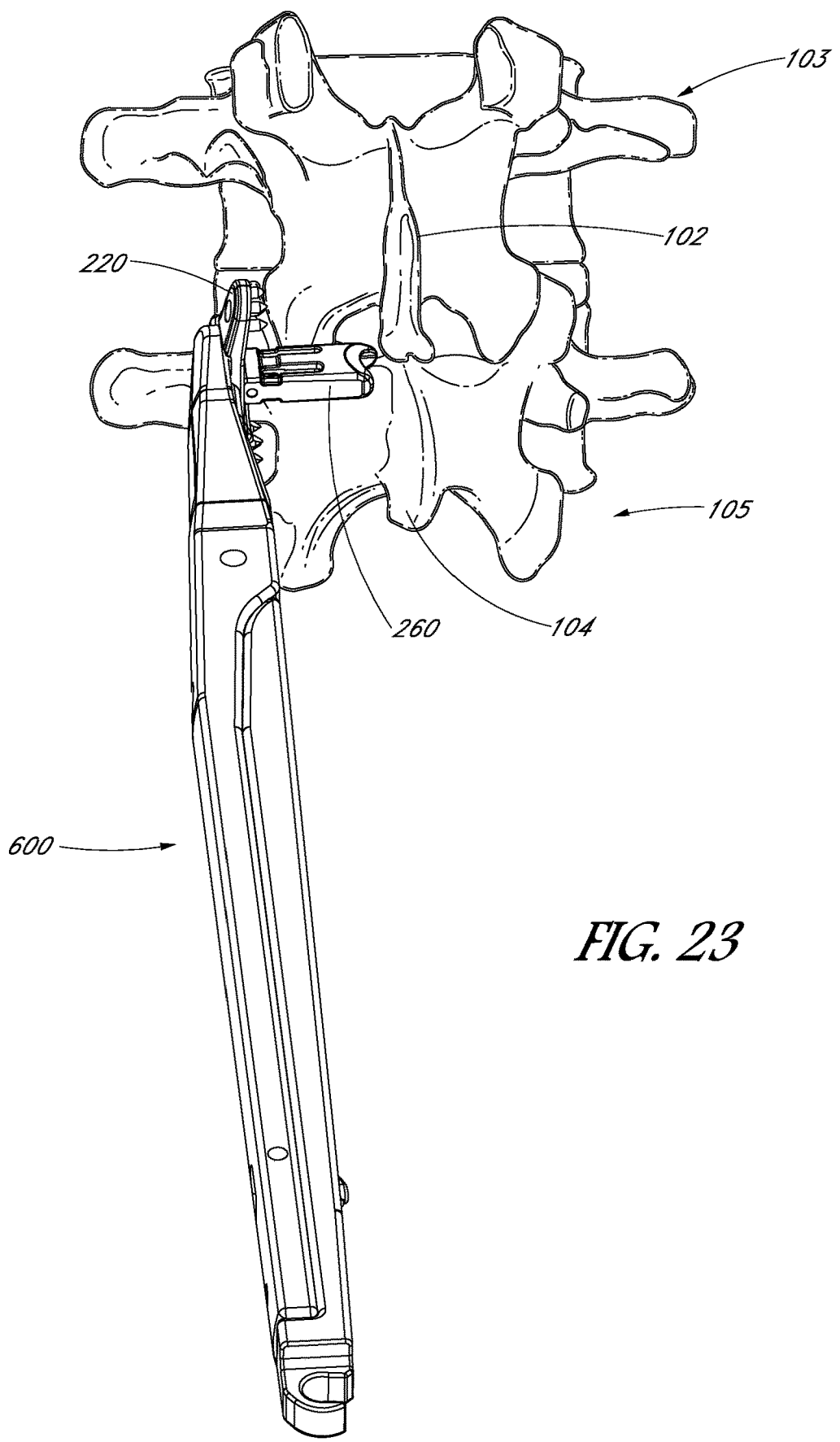
FIG. 23 illustrates the first inserter component of FIG. 15 with a first portion of an interspinous process device advanced to an implant site.

With reference to FIG. 23, the first inserter component 600 can be inserted to the implant site from a posterior approach. The first inserter component 600 that is coupled to the assembly with the first plate 120, 220 and the transverse member 160, 260, can be inserted into the incision, or one of the incisions, toward the area between a superior vertebra 103 and an inferior vertebra 105. The assembly can be positioned adjacent a superior spinous process 102 and an inferior spinous process 104.

Figure 24:
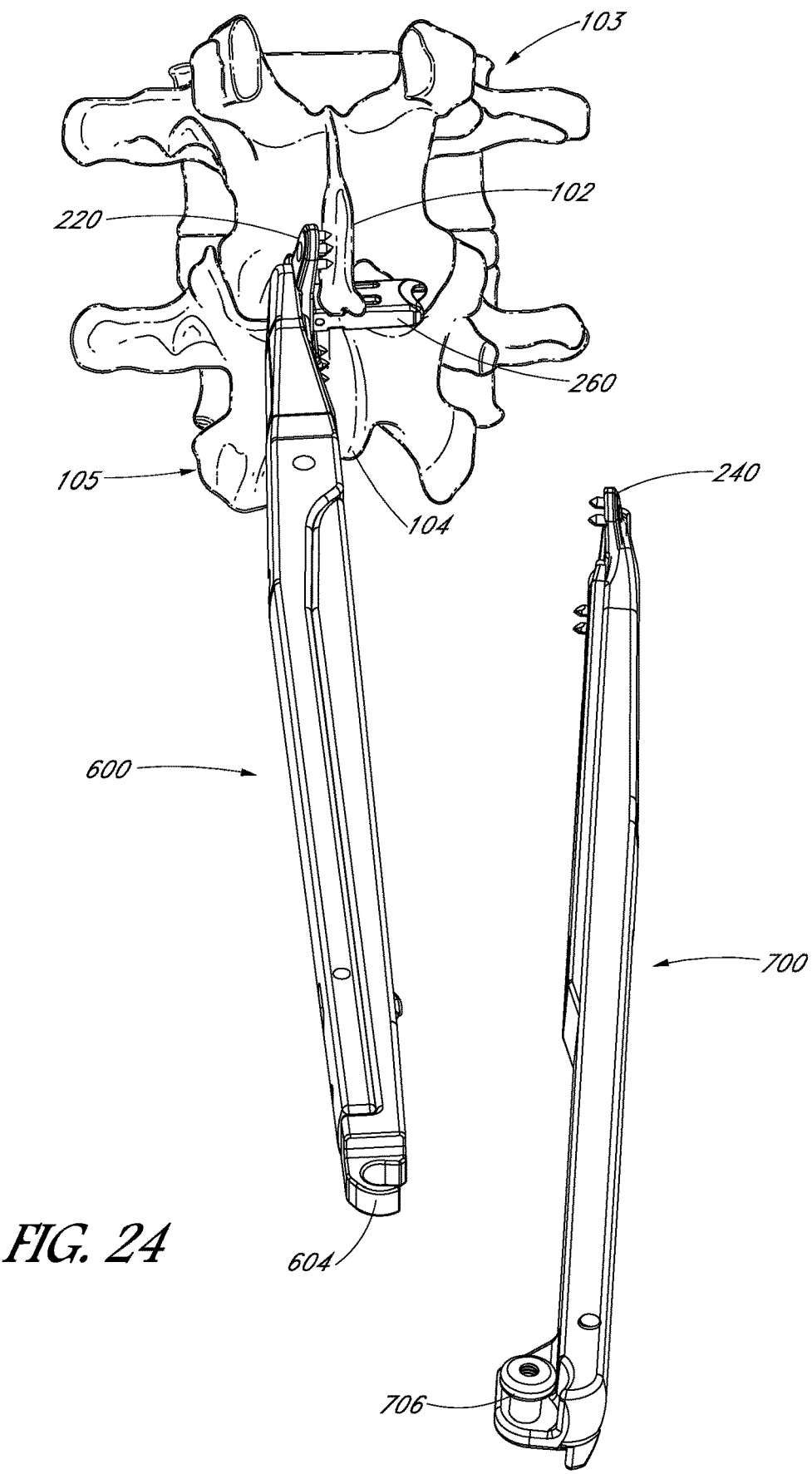
FIG. 24 illustrates the first inserter component of FIG. 15 with a first portion of an interspinous process device at an implant site and the second inserter component of FIG. 18 with a second portion of an interspinous process device advanced to the implant site.

The transverse member 160, 260 can be inserted between the spinous processes 102, 104, from one side of the spinous processes through the interspinous space and out the opposite side of the spinous processes, as illustrated in FIG. 24. In some embodiments, the transverse member 160, 260 is positioned under the supraspinous ligament without cutting or removing the supraspinous ligament. In some embodiments, the transverse member 160, 260 is oriented such that the smaller width extends from the superior spinous process 102 to the inferior spinous process 104. For example, the first surface 174 can be facing the superior spinous process and the second surface 176 can be facing the inferior spinous process. Once the transverse member 160, 260 is passed through the interspinous space, the transverse member 160, 260 can be rotated such that the larger width extends between the spinous processes 102, 104. For example, the transverse member 160, 260 can be oriented such that the openings 170 are facing the spinous processes 102, 104. The bone growth material in the openings 170 can beneficially help the bone to grow into the transverse member 160, 260 on the superior and inferior sides and help the device 100, 200 to fuse with the spine.

In some embodiments, the transverse member is expandable wherein the transverse member can be in a contracted configuration for easier implantation to the implant site. After delivering the interspinous process device to the implant site, the transverse member can be converted to an expanded configuration that has a width greater than the width in the contracted configuration in order to distract and/or maintain the desired distance between the superior and inferior spinous processes.

The second plate 140, 240 can be coupled to the second inserter component 700 by engaging the first finger 720 and second finger 722 with the tool engagement features 152, 252 on the second plate 140, 240. The actuator 710 can be manipulated to activate the actuation lever 712 and secure the first and second fingers 720, 722 to the second plate 140, 240.

Figure 25:
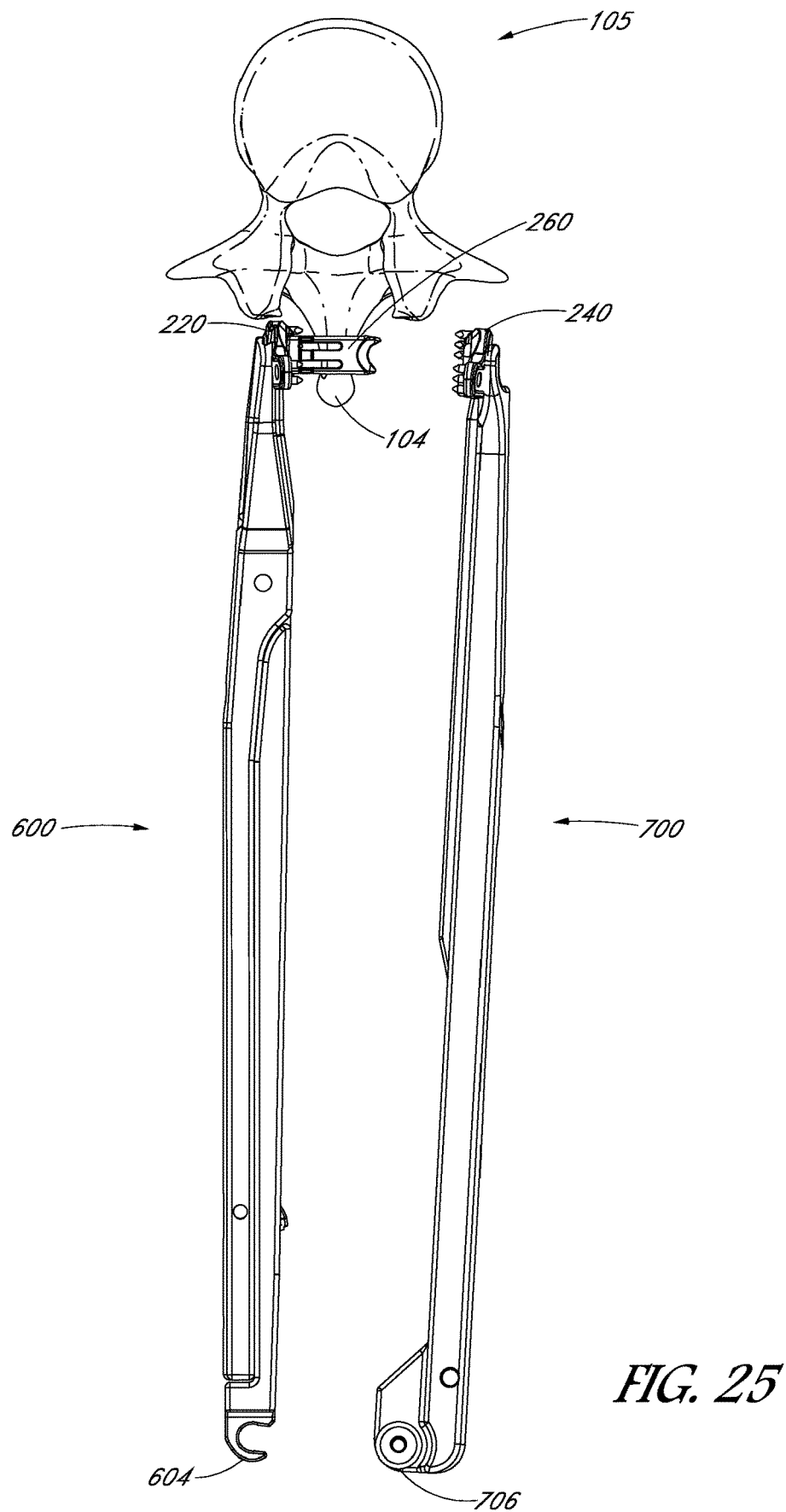
FIG. 25 illustrates the first inserter component of FIG. 15 with a first portion of an interspinous process device at an implant site and the second inserter component of FIG. 18 with a second portion of an interspinous process device near the implant site.

With continued reference to FIG. 24, the second inserter component 700 with the attached second plate 140, 240 can be inserted to the implant site from a posterior approach. The second inserter component 700 can be inserted into the same incision as the first inserter component 600, or a different incision, and advanced to the vertebrae toward the opposite side of the spinous processes as the first inserter component 600. FIG. 25 illustrates the first inserter component 600 and the second inserter component 700 in position near the spinous processes. FIG. 25 is a top view in the cranial to caudal direction showing the inferior vertebra 105 and inferior spinous process 104. The superior vertebra 103 is not shown for clarity.

Figure 26:
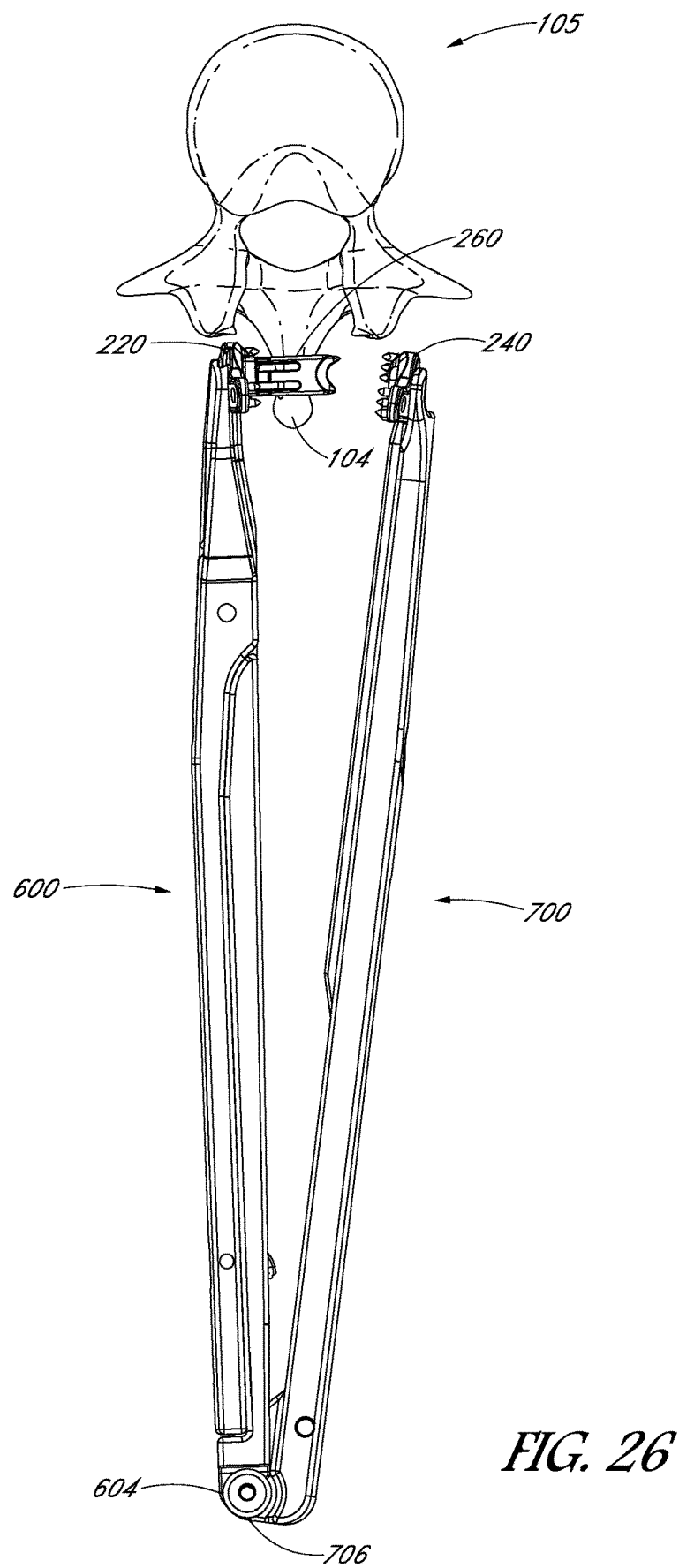
FIG. 26 illustrates a proximal end of the first inserter component of FIG. 15 coupled to a proximal end of the second inserter component of FIG. 18.

FIG. 26 illustrates the assembly having the first plate 120, 220 and transverse member 160, 260 on one side of the spinous processes and the second plate 140, 240 on the other side of the spinous processes. The first inserter component 600 is connected at the first hinge connector 604 with the second hinge connector 706 of the second inserter component 700. Coupling the first inserter component 600 with the second inserter component 700 can aid in assembling the interspinous process 100, 200. The hinged connection helps to align the transverse member 160, 260 with the aperture 242 on the second plate 240 for easier assembly, particularly at the implant site where visualization can be limited.

Figure 27:
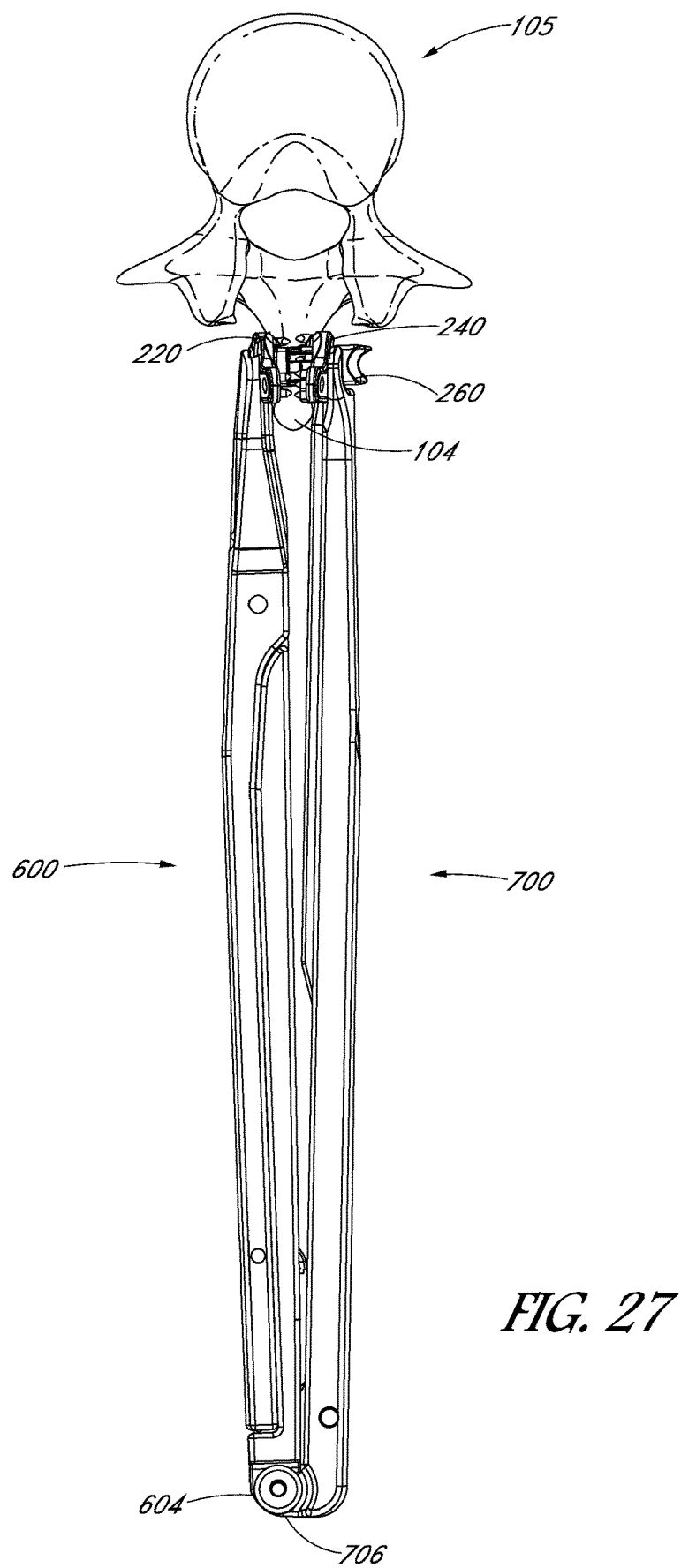
FIG. 27 illustrates the assembled inserter device of FIG. 26 coupling a first portion of an interspinous process device with a second portion of an interspinous process device at the implant site.

The first inserter component 600 and the second inserter component 700 can be squeezed together to introduce the second plate 140, 240 onto the transverse member 160, 260, as illustrated in FIG. 27. The second plate 140, 240 can be coupled with the transverse member 160, 260 on the spinous processes 102, 104 without initially tightening the fastener 192, 292.

Figure 28:
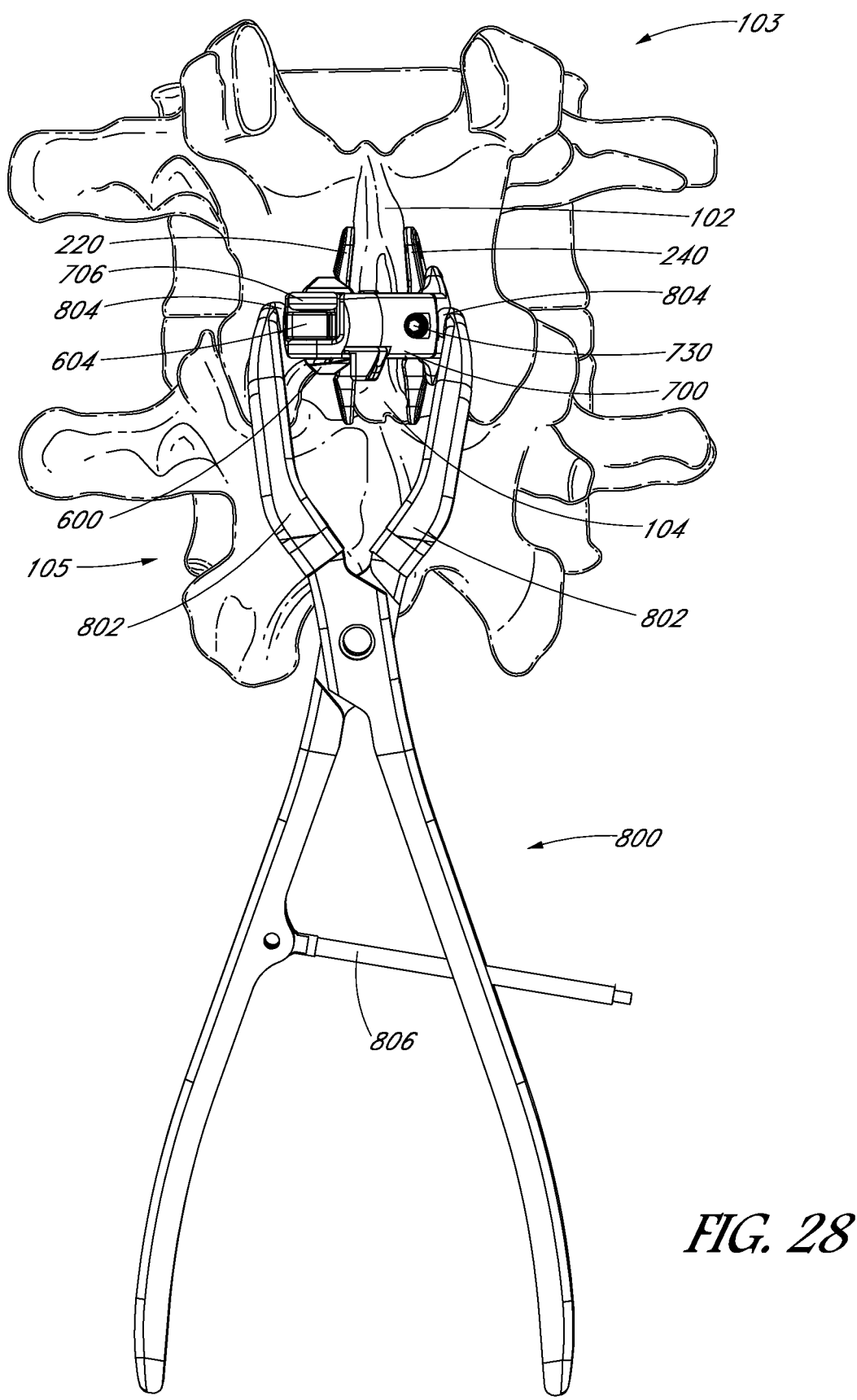
FIG. 28 is a view from the proximal end of the inserter device of FIG. 26, illustrating a compressor tool coupled to the inserter device.

A compression tool 800 can be used to squeeze the first plate 120, 220 and the second plate 140, 240 together against the spinous processes 102, 104, as illustrated in FIG. 28. In some embodiments, the compression tool 800 can be a plier-like tool with a compressor arm 802 configured to engage the first plate 120, 220 and a second compressor arm 802 configured to engage the second plate 140, 240. The compressor arms 802 can have tips 804 that are configured to engage the first plate 120, 220 and the second plate 140, 240. For example, the tips 804 can be ball-shaped engagement ends configured to fit in the depressions 134 of the first plate 120, 220 and the depressions 154 of the second plate 140, 240. The tips 804 can also be configured to couple with complementary features on the first inserter component 600 and the second inserter component 700. When the compression tool 800 is actuated, the first plate 120, 220 and second plate 140, 240 are moved toward each other onto the spinous processes 102, 104. The first plates 120, 220 and second plates 140, 240 can have spikes, or other engagement feature as described above, that engage the sides of the spinous processes 102, 104. In some embodiments, the spikes 136, 156 can pierce the sides of the spinous processes 102, 104. The compression tool 800 can have a locking member 806 that can maintain the compressor arms 802 in a compressed position. For example the locking member 806 can be a ratcheting mechanism that allows the compressor arms 802 to move toward each other, but prevents the arms 802 from moving apart. In other embodiments, the locking member 806 can be a threaded shaft with a nut that can be tightened against one of the arms 802 to prevent the arms 802 from moving apart. In some embodiments, the compression tool can be used to also provide the preload to the interspinous process device.

After the first plate 120, 220 and second plate 140, 240 are pressed together in a desired compressed configuration, a drive tool 900 can be used to engage the fastener 194, 294 and lock the device 100, 200 to the spinous processes 102, 104. The drive tool 900 can have a drive handle 902 at the proximal end and a long drive shaft 904 with a fastener engagement at the distal end. The drive tool 900 can be inserted into the access channel 730 of the second inserter component 700 to access the fastener 194, 294 on the second plate 140, 240, as illustrated in FIG. 29. The drive shaft 904 is preferably sufficiently long to extend from the fastener to outside the surgical incision. In some embodiments, the drive tool can be a torque drive that can limit the amount of torque applied to the fastener 194, 294. As mentioned before, the second plate 140, 240 can have some adjustability even after the fastener 194, 294 is tightened, which can help the second plate 140, 240 conform to the spinal anatomy of the patient. The first plate 120, 220 can also have some adjustability. The spring mechanism 190 can allow the first plate 120, 220 to pivot and angle to conform to the spinal anatomy of the patient.

The compression tool 800, first inserter component 600 and the second inserter component 700 can be released after the fastener 194, 294 is tightened. To remove the compression tool 800, the locking member 806 can be released. Then the first inserter component 600 can be detached from the second inserter component 700 by separating the first hinge connector 604 from the second hinge connector 706. To remove the second inserter component 700, the actuator 710 can be activated to release the fingers 720, 722 from the second plate 140, 240. The first inserter component 600 can be removed from the first plate 220 by releasing the latch 606 to separate the first arm 610 and second arm 620, allowing the first plate engagement 616 to separate from the first plate 120, 220.

In some embodiments, the first plate 120, 220, the second plate 140, 240, the transverse member 160, 260, the post 180, 280 and the spring mechanism 190 are preassembled prior to being inserted into the patient. One or more of the orifice 172, openings 170 and the outer surfaces of the transverse member 160, 260 can have bone growth material, such as allograft or DBM. The second plate 140, 240 can be slideably assembled to the transverse member 160, 260 but not yet fixed so that the position of the second plate 140, 240 can be adjusted. The assembly can be delivered from a posterior approach to the interspinous space. In such embodiments, the supraspinous ligament is cut and/or removed to provide access to the interspinous space. The assembly can be delivered so that the first plate 120, 220 is on one side of the spinous processes and the second plate 140, 240 is on the opposite side of the spinous processes. In some embodiments, the transverse member 160, 260 is oriented during implantation such that the smaller width extends from the superior spinous process to the inferior spinous process. For example, the first surface 174 can be facing the superior spinous process 102 and the second surface 176 can be facing the inferior spinous process 104. Once the transverse member 160, 260 is positioned in the interspinous space, the transverse member 160, 260 can be rotated such that the larger width extends between the spinous processes. For example, the transverse member 160, 260 can be rotated such that the openings 170 are facing the spinous processes. The bone growth material in the openings 170 can beneficially help the bone to grow into the transverse member 160, 260 on the superior and inferior sides and help the device 100, 200 to fuse with the spine.

In some embodiments, the second inserter component 700 can be a preload tool that is coupled to tool engagement features 132 on the first plate 120, 220. The tool can be actuated to apply a preload on the spring mechanism 190. In some embodiments, the tool can be locked in the actuated configuration so that the preload can be applied without having to hold the tool. A compression tool 800 can also be used to squeeze the first plate 120, 220 and the second plate 140, 240 together against the spinous processes. When the compression tool 800 is actuated, the first plate 120, 220 and second plate 140, 240 are moved toward each other onto the spinous processes. The first plate 120, 220 and second plate 140, 240 can have spikes, or other engagement feature as described above, that engage the sides of the spinous processes. In some embodiments, the spikes 136, 156 can pierce the sides of the spinous processes. In some embodiments, a single tool can be used that performs the function of both the preload tool and the compression tool.

After the plates are pressed together, a drive tool 900 can be used to engage the fastener 194, 294 and lock the device 100, 200 to the spinous processes. The compression tool 800, the first inserter component 600 and second inserter component 700 can be released after the fastener 194, 294 is tightened. As mentioned before, the second plate 140, 240 can have some adjustability even after the fastener 194, 294 is tightened, which can help the second plate 140, 240 conform to the spinal anatomy of the patient. The first plate 120, 220 can also have some adjustability. The spring mechanism 190 can allow the first plate 120, 220 to pivot and angle to conform to the spinal anatomy of the patient.

In some instances, a spinal implant can become loosened from the implant site for a variety of reasons, such as due to patient movement and flexion of the implant. For example, the interspinous process device may dig into the spinous processes and settle into the implant site, causing loosening of the compression of the plates applied during the implant procedure. In the interspinous process device disclosed herein, the first and second plates advantageously have a preload force provided by the spring mechanism that urges the plates together. This preload force can take up the slack and account for the loosening of the plates and help maintain the interspinous process device on the spinous processes, resulting in improved fusion time and efficacy.

In some embodiments, one or more components of the interspinous process device 100, 200 can be implanted from a lateral approach or a posterolateral approach. For example, the assembly with the first plate 120, 220 and transverse member 160, 260 can be delivered from a lateral approach to the interspinous space while the second plate 140, 240 is delivered from a posterior approach.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. An interspinous process device comprising:
   a first plate;
   a second plate comprising an aperture;
   a transverse member between the first plate and the second plate, wherein the transverse member is configured to fit through the aperture of the second plate, wherein the first plate is not directly connected to the transverse member;
   a post coupled to the transverse member;
   a fastener through the second plate configured to fix the position of the second plate along the transverse member, wherein the fastener does not engage the post; and
   a spring mechanism between the post and the first plate, wherein the spring mechanism is configured to urge the first plate and the second plate together to help maintain compression of the interspinous process device.

2. The device of claim 1, wherein the spring mechanism is comprised of at least one washer.

3. The device of claim 1, wherein the transverse member comprises a hollow chamber and at least one opening on a side wall of the transverse member that is in fluid communication with the hollow chamber.

4. The device of claim 1, further comprising the post disposed through a hole in the first plate and coupled to the transverse member.

5. The device of claim 1, wherein the post is attached to the transverse member between the first plate and the second plate.

6. The device of claim 1, wherein the post resides within the transverse member.

7. The device of claim 1, wherein the post is attached to the transverse member with a fastener.

8. An interspinous process device comprising:
   a first plate;
   a second plate;
   a transverse member between the first plate and the second plate, wherein the second plate is configured to translate along a length of the transverse member, wherein the first plate is not directly connected to the transverse member;

a post coupled to the transverse member, wherein the post does not extend to the second plate; and a spring mechanism between the post and the first plate, wherein the spring mechanism is configured to urge the first plate and the second plate together to help maintain compression of the interspinous process device.

9. The device of claim 8, further comprising a fastener on the second plate that tightens on the transverse member.

10. The device of claim 8, wherein a first surface of the transverse member has an angle with respect to a second opposite surface of the transverse member.

11. The device of claim 10, wherein the angle is at least approximately 0.1 degree and/or less than or equal to approximately 7 degrees.

12. The device of claim 10, wherein the angle is at least approximately 0.1 degree and/or less than or equal to approximately 3 degrees.

13. The device of claim 8, wherein the spring mechanism is comprised of at least one washer.

14. The device of claim 8, wherein at least a portion of the device has a coating made of one or more of titanium and hydroxylapatite.

15. The device of claim 8, wherein the transverse member comprises a hollow chamber and at least one opening on a side wall of the transverse member that is in fluid communication with the hollow chamber.

16. The device of claim 8, further comprising the post disposed through a hole in the first plate and coupled to the transverse member.

17. An interspinous process device comprising:

a first plate;

a second plate;

a transverse member between the first plate and the second plate, wherein the second plate is configured to translate along a length of the transverse member, wherein the first plate is not directly connected to the transverse member;

a post coupled to the transverse member away from the second plate;

a fastener configured to fix the position of the second plate along the transverse member without engaging the post; and a spring mechanism between the post and the first plate, wherein the spring mechanism is configured to urge the first plate and the second plate together to help maintain compression of the interspinous process device.

18. The device of claim 17, wherein the transverse member comprises a chamber configured to hold material to assist bone growth.

19. The device of claim 17, further comprising spikes on the first plate and spikes on the second plate, wherein the spikes on the first plate are not aligned with the spikes on the second plate.

* * * * *